US011771303B2

(12) United States Patent
Williams

(10) Patent No.: US 11,771,303 B2
(45) Date of Patent: Oct. 3, 2023

(54) SYSTEM AND METHOD FOR WIRELESSLY TRANSMITTING OPERATIONAL DATA FROM AN ENDOSCOPE TO A REMOTE DEVICE

(71) Applicant: Integrated Medical Systems International, Inc., Birmingham, AL (US)

(72) Inventor: Dawn R. Williams, Colleyville, TX (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 168 days.

(21) Appl. No.: 17/507,386

(22) Filed: Oct. 21, 2021

(65) Prior Publication Data
US 2022/0039634 A1    Feb. 10, 2022

Related U.S. Application Data

(60) Continuation of application No. 16/774,473, filed on Jan. 28, 2020, now abandoned, which is a division of
(Continued)

(51) Int. Cl.
*A61B 1/00* (2006.01)
*A61B 1/05* (2006.01)
*A61B 1/06* (2006.01)

(52) U.S. Cl.
CPC ...... *A61B 1/00016* (2013.01); *A61B 1/00009* (2013.01); *A61B 1/00032* (2013.01);
(Continued)

(58) Field of Classification Search
CPC ............ A61B 1/00002; A61B 1/00004; A61B 1/00009; A61B 1/00011; A61B 1/00016;
(Continued)

(56) References Cited

U.S. PATENT DOCUMENTS 3,945,371 A    3/1976  Adelman
7,902,990 B2   3/2011  Delmonico et al.
(Continued)

FOREIGN PATENT DOCUMENTS

CN    201948981 U    8/2011
CN    203468574 U    3/2014
(Continued)

*Primary Examiner* — Alexandra L Newton
(74) *Attorney, Agent, or Firm* — James H. Ortega; Carstens, Allen & Gourley, LLP

(57) ABSTRACT

A system for wirelessly transmitting data from an endoscope, comprising an endoscope having a control body, an insertion tube extending from the control body, the distal end of the insertion tube containing an image sensor and a light source, and a control head connected to the control body, which comprises a battery; a light source amplifier connected to the battery, the light source amplifier operable to boost the intensity of the light source; a video processor configured to create compressed video data from a video stream captured via the image sensor; and a wireless communication module configured to negotiate a wireless connection with a mobile device, wherein the wireless communication module is further configured to transmit the compressed video data to the mobile device over the wireless connection, and wherein the wireless communication module comprises a channel discriminator configured to automatically avoid RF interference.

18 Claims, 16 Drawing Sheets

Related U.S. Application Data application No. 14/508,265, filed on Oct. 7, 2014, now abandoned.

(60) Provisional application No. 61/998,690, filed on Jul. 7, 2014.

(52) U.S. Cl.
CPC ...... *A61B 1/00042* (2022.02); *A61B 1/00048* (2013.01); *A61B 1/00108* (2013.01); *A61B 1/05* (2013.01); *A61B 1/0676* (2013.01)

(58) Field of Classification Search
CPC ............ A61B 1/00039; A61B 1/00041; A61B 1/00043; A61B 1/00045
See application file for complete search history.

(56) References Cited

U.S. PATENT DOCUMENTS

| | | |
|---|---|---|
| 8,558,880 B2 | 10/2013 | Nambakam et al. |
| 2006/0106280 A1 | 5/2006 | Surti et al. |
| 2009/0209810 A1 | 8/2009 | Endo et al. |
| 2011/0034769 A1* | 2/2011 | Adair ................... H04N 23/54 600/110 |
| 2011/0190579 A1 | 8/2011 | Ziarno et al. |
| 2011/0315567 A1 | 12/2011 | Boynton et al. |
| 2012/0112690 A1 | 5/2012 | Stulen et al. |
| 2012/0289858 A1* | 11/2012 | Ouyang ................ A61B 1/045 600/562 |
| 2013/0102930 A1 | 4/2013 | Connor |
| 2014/0221740 A1 | 8/2014 | Kawula et al. |
| 2014/0275763 A1 | 9/2014 | King et al. |
| 2015/0099458 A1 | 4/2015 | Weisner et al. |
| 2015/0297062 A1 | 10/2015 | Golenberg et al. |
| 2016/0213236 A1 | 7/2016 | Hruska et al. |
| 2017/0280988 A1* | 10/2017 | Barbato ................ A61B 1/317 |

FOREIGN PATENT DOCUMENTS

| | | |
|---|---|---|
| EP | 2106143 A1 | 9/2009 |
| EP | 2493193 A1 | 8/2012 |
| KR | 20120008059 U | 11/2012 |

\* cited by examiner

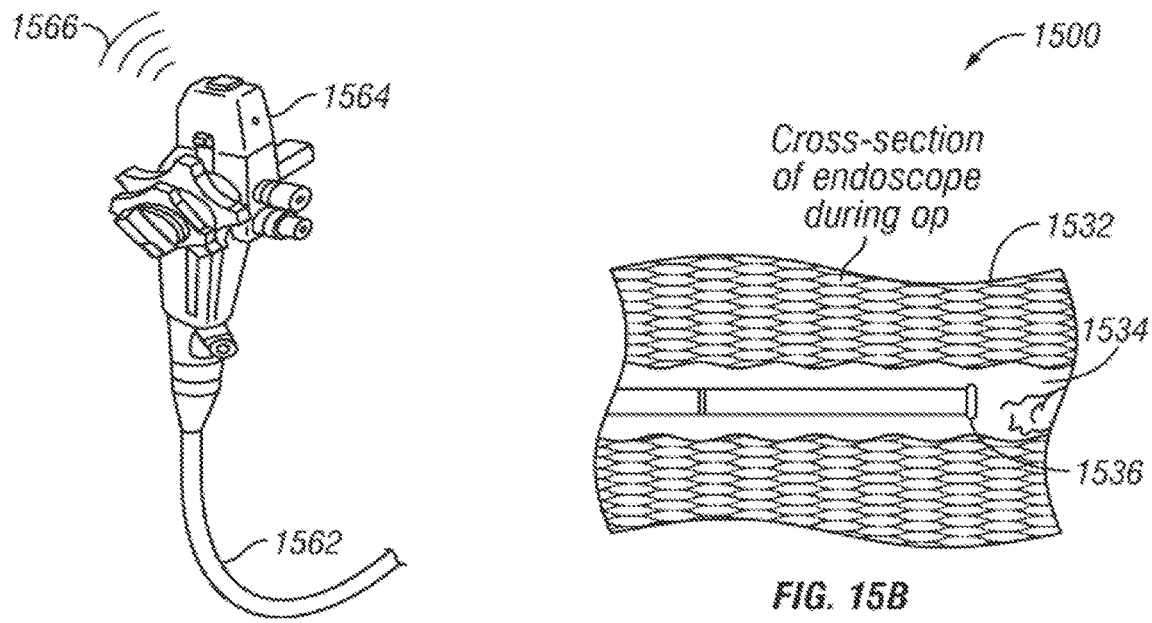
FIG. 15A
FIG. 15B
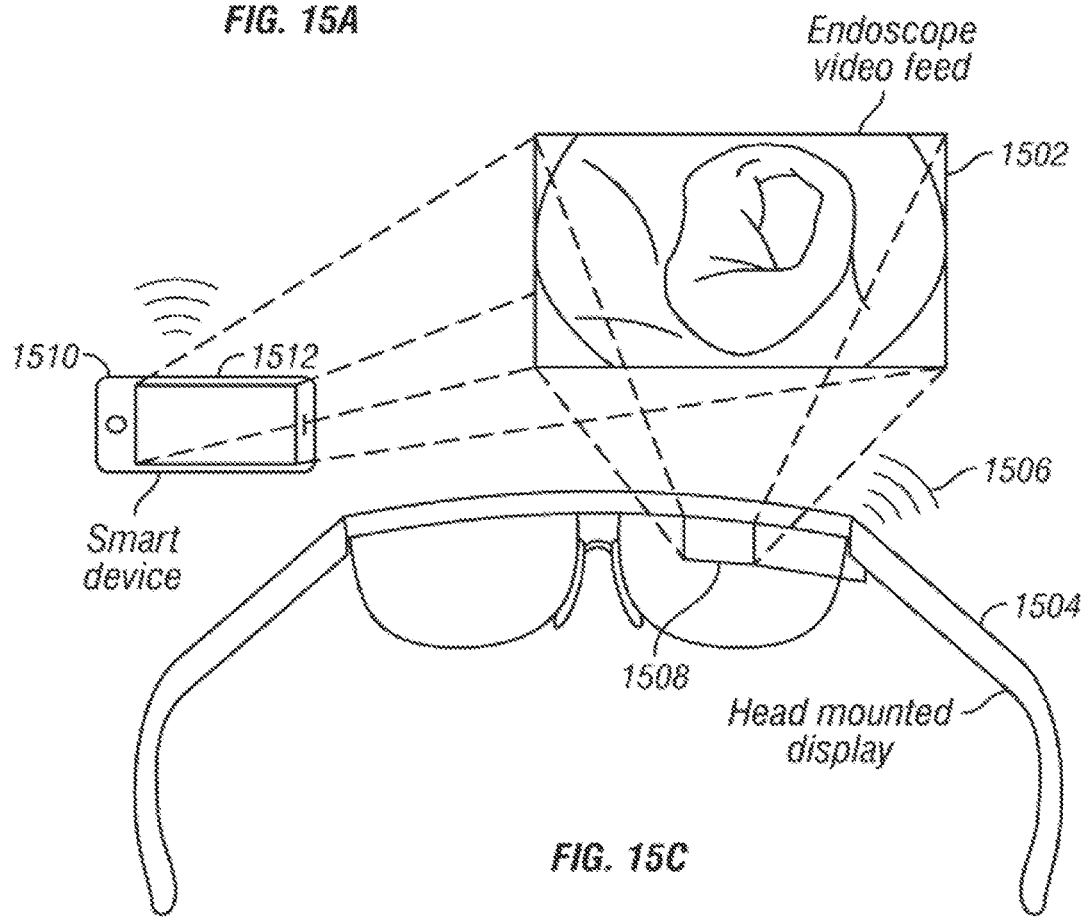
FIG. 15C

SYSTEM AND METHOD FOR WIRELESSLY TRANSMITTING OPERATIONAL DATA FROM AN ENDOSCOPE TO A REMOTE DEVICE

CROSS-REFERENCE TO RELATED APPLICATIONS

This disclosure is a continuation application of U.S. application Ser. No. 16/774,473, filed Jan. 28, 2020, which is a divisional application of U.S. application Ser. No. 14/508,265, filed Oct. 7, 2014, which claims the benefit of U.S. Provisional Application No. 61/998,690, filed Jul. 7, 2014.

BACKGROUND OF THE INVENTION

1. Field of the Invention

This invention relates in general to the field of medical devices, and more particularly to a system and method for wirelessly transmitting operational data from an endoscope to a remote device.

Doctors and veterinarians rely on a bevy of medical imaging technologies, including x-rays, x-ray fluoroscopy, magnetic resonance imaging (MRI), and CT/PET scans to obtain different views of a patient's symptoms and anatomy. However, for some conditions, it may be advantageous or necessary to gather real-time operational data from inside the body by relying on a device known as an endoscope.

Endoscopes can be used in a variety of medical procedures. For example, an endoscope may be used to investigate symptoms in the digestive system by searching for the source of abdominal pain or gastrointestinal bleeding. Endoscopes may also be used to confirm a diagnosis, most commonly by performing a biopsy to check for inflammation and cancers of the digestive system. Additionally, treatments may be administered via an endoscope, such as cauterization of a bleeding vessel, widening a narrow esophagus, clipping off a polyp, or removing a foreign object.

During an endoscopy procedure or examination, an endoscope tube is inserted into a body cavity, such as: the stomach, duodenum, small intestine or large intestine. The insertion tube contains an optical device and a light source that allows the examiner to view the inside of the body cavity via an eyepiece or wired monitor.

2. Description of Related Art

FIG. 1 shows an example of a complete endoscopy system, indicated generally at 100, as it is used in most cases today. The endoscope described above would typically be supported by a wired monitor 108, wired light source, wired video processor 116, wired recorder, and a wired printer 112. The typical dimension for this complete tower is three feet in width by 6 feet in height. The light source and video processor 116 are hard-wired to the endoscope via a cable 118 that contains one entry point at one end that connects to the endoscope 102 and a dual entry point (not depicted) at the other end that allows connection to the video processor 116 and light source.

In the case where a wired monitor is used, the configuration illustrated in FIG. 1 is undoubtedly required. Such a configuration limits the usage of the endoscope to procedures conducted in the examiner's office due to the size and weight of the supporting equipment. Mobility is extremely limited due to its bulky nature. In most cases, the physical presence of the complete system 100 with its bulky componentry and cabling forces the owner to commit significant office area for usage and storage.

In configurations where an eyepiece is used, the position of the eyepiece requires the examiner to stand in close proximity of the patient. Additionally, this option, by itself, does not provide the capability to capture images and video, nor does it allow for printing or the possibility of other integrated functionality. Use with an eyepiece can also present unique challenges for veterinarians, who must stand in close proximity to an animal patient, which may become spooked during the operation.

FIG. 2 illustrates a portable wired videoscope, indicated generally at 200, which attempts to alleviate these shortcomings, among others, by replacing the eyepiece equipped endoscope with a display unit 208 wired 204 to the endoscope 202 stabilized by a grip 206. The display unit 208 interprets the signal from the endoscope camera (not shown), which is carried via a special-purpose, wired electronic interface 204. The endoscope body 202 conducts the camera lead wires and the light guide from the distal end of the insertion tube to the wired display unit 208. Any signal processing is conducted solely within the display unit 208. Such an encapsulated approach leads to expensive proprietary solutions that handcuff the display technology to the signal processing unit and preclude the substitution of other general purpose displays such as a smart device or tablet. Additionally, the videoscope 200 would still have to be wired to an external light source.

BRIEF SUMMARY OF THE INVENTION

In accordance with one aspect of the present invention, a system and method for wirelessly transmitting operational data from an endoscope to a remote device is provided which substantially eliminates or reduces disadvantages associated with previous systems and methods.

In accordance with one embodiment, a system is provided for wirelessly transmitting data from an endoscope, comprising an endoscope having a control body, an insertion tube extending from the control body and housing an image sensor and a light source in its distal end, and a control head connected to the control body, which comprises a battery, a light source amplifier connected to the battery, the light source amplifier, a video processor configured to create compressed video data from a video stream captured via the image sensor, and a wireless communication module configured to negotiate a wireless connection with a mobile device, wherein the wireless communication module is further configured to transmit the compressed video data to the mobile device over the wireless connection, and wherein the wireless communication module comprises a channel discriminator configured to automatically avoid RF interference. In particular embodiments, the present invention further includes a wireless communication module configured to negotiate a second wireless connection with a second mobile device and to simultaneously transmit the compressed video data to the second mobile device over the second wireless connection.

In accordance with another embodiment, a method is provided for sharing data on a mobile device wirelessly connected to an endoscope, comprising the steps of: establishing a wireless connection from a first device to a wireless endoscope, receiving video data on the first device from the wireless endoscope over the wireless connection, creating a symbol on the first device based on the video data received from the wireless endoscope, and transmitting the symbol to a second device connected to the wireless endoscope, the symbol to be displayed on the second device alongside the video data.

In accordance with yet another embodiment, a system is provided for transporting and charging the system of claim 1, comprising: a force damping system nested within a rigid outer shell, a cavity within the force damping system suitable to receive a stowed device, a charging interface, a transformer connected to the charging interface, a power management controller configured to manage charging of the stowed device, a power cord connected to the transformer, and a battery level indicator configured to monitor power status notifications from the stowed device. In particular embodiments, the present invention further includes charging coils operable to charge the stowed device using wireless induction.

One advantage of the present invention is its adaptability. For example, wireless transmission of operational data allows an examiner to monitor an ongoing operation using the examiner's personal device, such as: a smart phone, a tablet, a head-mounted display, or a monitor.

Remote monitoring of an endoscopy procedure provides yet another advantage of the many embodiments by enabling classrooms or seminars to participate in a live operation. This opens up new possibilities where only a passive review of prerecorded operations was previously possible. Clinical studies may be expanded beyond centralized operational facilities to remote sites, such as a battlefield, emergency clinic, or even a barn. When coupled with the operational data sharing method discussed in detail below, the remote networking capabilities enable new and useful telemedicine applications. For example, an experienced physician could oversee multiple concurrent off-site operations conducted by junior physicians, and provide operational feedback through his monitoring device.

Another advantage of the present invention is its portability. For human patients, endoscopy procedures are performed in centralized facilities, such as a hospital or clinic, where the equipment may be stored and operated. It is reasonable to expect a patient to travel to and from the facility to have the operation performed. However, for veterinarians performing similar operations, it is not cost effective to transport a large animal, such as a horse or a cow, to a clinic or animal hospital. This is especially true for large marine animals, such as a whale or dolphin. Accordingly, the relatively small footprint of the many embodiments enables veterinarians to travel off-site to perform endoscopy operations. Furthermore, it enables veterinarians to schedule the examination of multiple animals at the same site, or schedule multiple operations in the same day and travel from site to site.

In order to achieve the main objective, the present invention is directed to the satisfaction of the capabilities required from a conventional endoscope comprising a main body, an insertion tube, valves connected to guide channels to support air, water, and therapeutic instruments, therapeutic instrument insertion port, and angulation knobs and componentry; all of which comprise an existing FDA approved medical device.

BRIEF DESCRIPTION OF THE SEVERAL VIEWS OF THE DRAWINGS

For a more complete understanding of the present invention and its advantages, reference is now made to the following description and the accompanying drawings, in which:

FIGS. 15A, 15B, and 15C show several views illustrating the wireless transmission of operational data to a variety of devices;

DETAILED DESCRIPTION OF THE INVENTION

Figure 1:
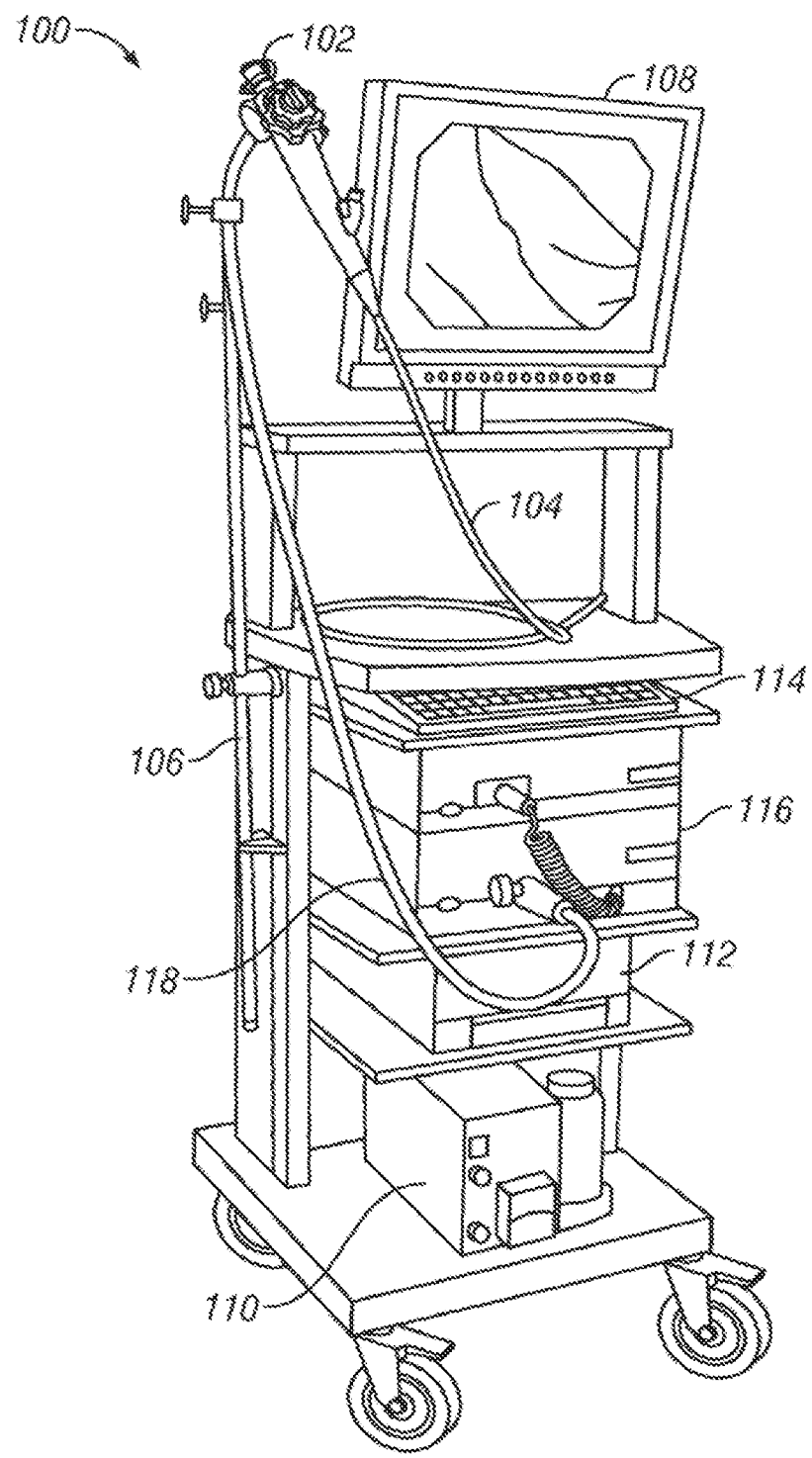
FIG. 1 illustrates a conventional video endoscope tethered to a monitoring station.
Figure 2:
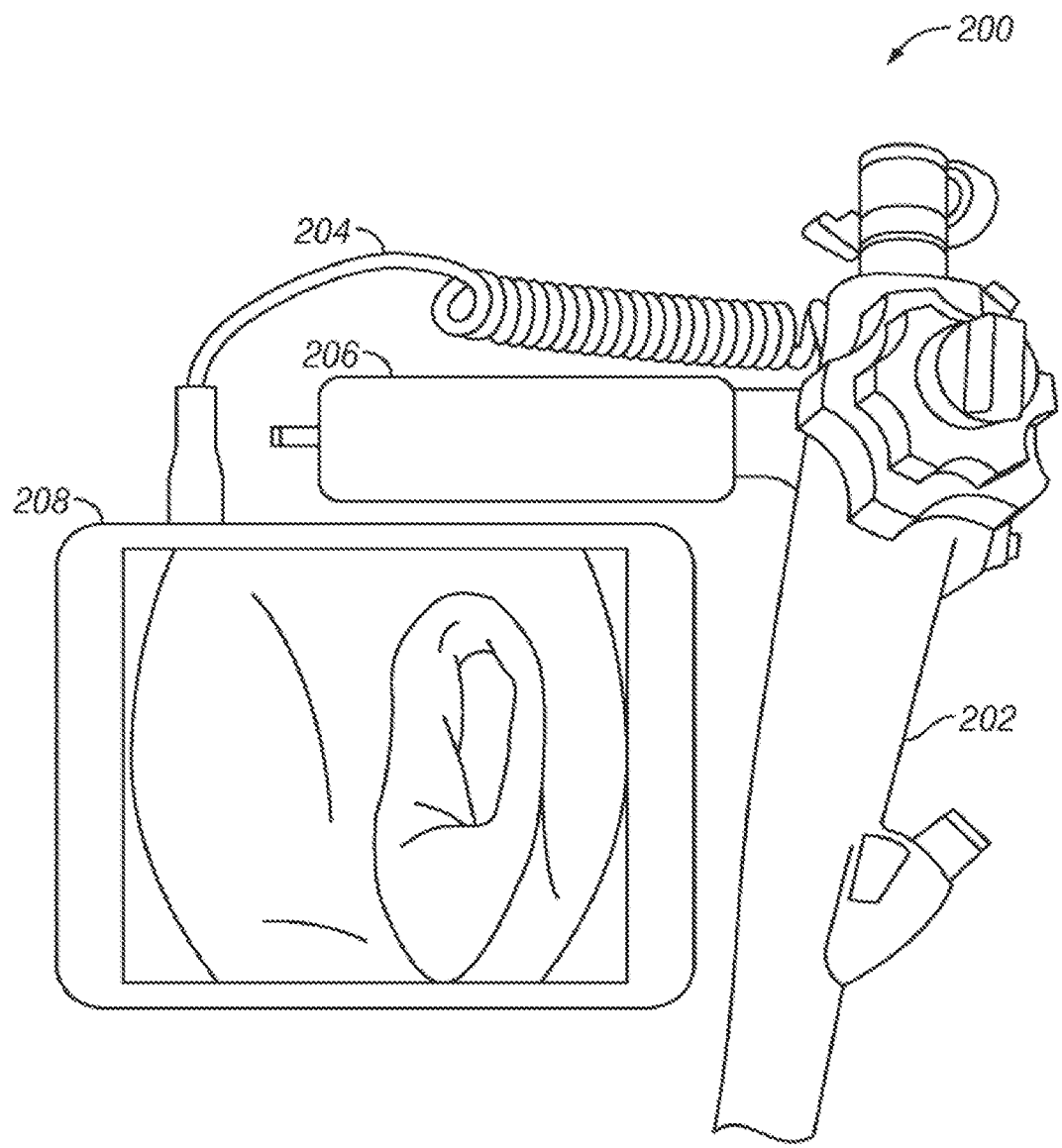
FIG. 2 illustrates a portable video endoscope wired to a specially designed monitoring device.

Referring to the drawings, embodiments of the present invention will be described below.

Figure 3:
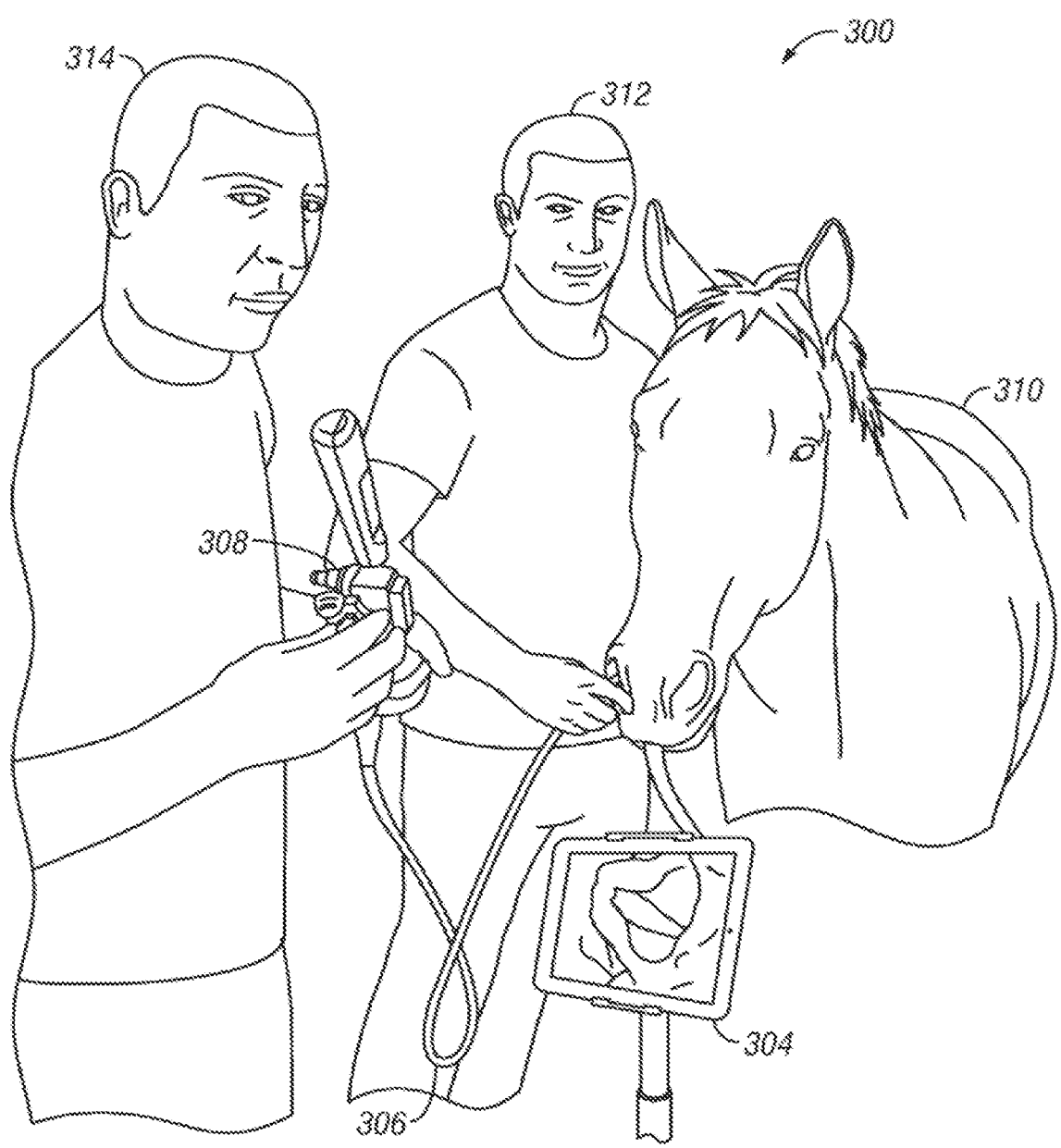
FIG. 3 illustrates a veterinary endoscopy examination using a wireless endoscope connected to a mobile device.

FIG. 3 illustrates a respiratory endoscopy examination being performed on a horse, indicated generally at 300, using a wireless endoscope 308 connected to a mobile device 304 in accordance with one embodiment. As FIG. 3 demonstrates, wireless endoscopy is particularly useful in applications where a patient is not fully sedated or restrained. During an operation, the insertion tube 306 of the wireless endoscope 308 is introduced into the horse's 310 respiratory system via its nostril. Attendant 312 stabilizes the horse 310 and guides the insertion tube 306 during the operation. The veterinarian 314 observes the operation on the display 304, which may be supported by a tripod or stand, while controlling the endoscope 308.

If a veterinary patient, such as a horse, becomes spooked during an operation, the absence of wires can reduce trauma to the animal, which has less equipment attached to it, as well as minimize harm to attending persons and equipment. Likewise, a wireless operating environment eliminates tripping hazards, which can be a common source of physician injury during operations. Such injuries are especially commonplace during laparoscopic inseminations of game animals, which are often conducted on multiple animals simultaneously with wires crisscrossing the floor of the operating environment.

Figure 4A:
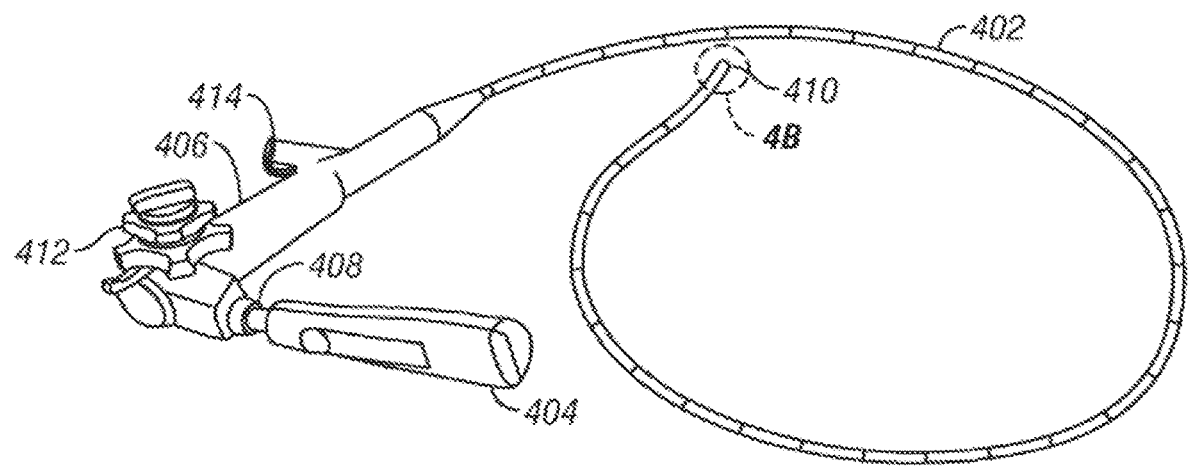
FIG. 4A illustrates a perspective view of a wireless endoscope featuring a flexible insertion tube in accordance with one embodiment.

FIG. 4A illustrates a perspective view of a wireless endoscope featuring a flexible insertion tube in accordance with one embodiment. The wireless endoscope is comprised of a wireless control head 404, a control body 406, and a flexible insertion tube 402. The endoscope control body 406 features a biopsy port 414 and angulation knobs 412, which manipulate the distal end 410 of the flexible insertion tube 402. The wireless control head 404 attaches to the control body 406 via a mechanical coupling that houses an electronic data/control interface 408 (described in further detail in FIGS. 9 and 13). The data interface connects to the optical system, which originates in the control body and extends to the distal end 410 of the flexible insertion tube 402. The control body 406 may include a light source (usually an LED), which transfers the light to the distal end 410 of the insertion tube via a fiber optic light guide bundle. Alternatively, the light source may be located in the distal end of the insertion tube and powered by the wireless control head 404 via the data/control interface 408.

Figure 4B:
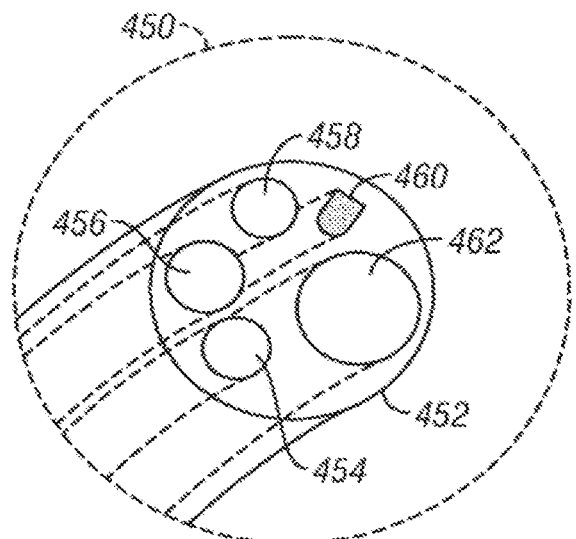
FIG. 4B illustrates an enlarged perspective view of the distal end of a flexible insertion tube.

FIG. 4B illustrates an enlarged perspective view of the distal end assembly 410 of a flexible insertion tube 402, indicated generally at 450, that includes a channel for air and water 458, a water nozzle 460, an optical system 462, optional suction 454, and a biopsy channel 456. The distal end assembly 410 is enclosed with a cap 452 that works in conjunction with the insertion tube 402 to seal the endoscope instruments from fluids. As illustrated, the optical system comprises a light source and a camera combined into one lens system; however, alternative embodiments may separate the light source and camera across different channels within the insertion tube.

In operation, the angulation knobs 412 manipulate the distal end 410 so as to direct the optical system. A light lens focuses light from the light source onto a subject within the body. A camera lens then focuses the light reflected from the illuminated subject onto an image sensor (e.g., a CCD, CMOS, NMOS, or PMOS image sensor) housed in the distal end 410. The image sensor records the captured light as image or video data and transmits it to the control head 404 via lead wires that run from the distal end 410 to the control body 406 and terminate at the data/control interface 408. If fluids or other body matter obstruct the optical system 462, a nozzle 460 can be used to direct air or water to clear the obstruction.

Figure 5:
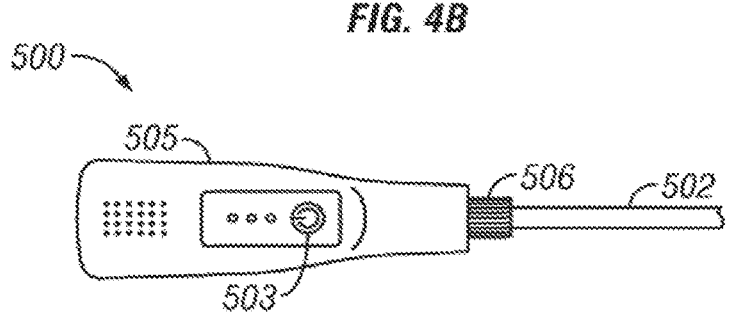
FIG. 5 illustrates a side view of a wireless endoscope with a rigid insertion tube.

FIG. 5 illustrates a side view of a wireless endoscope with a rigid insertion tube, indicated generally at 500. The wireless endoscope 500 is comprised of a control head 505, a control button 503, a rigid insertion tube 502, and a sheath lock 506.

Figure 6:
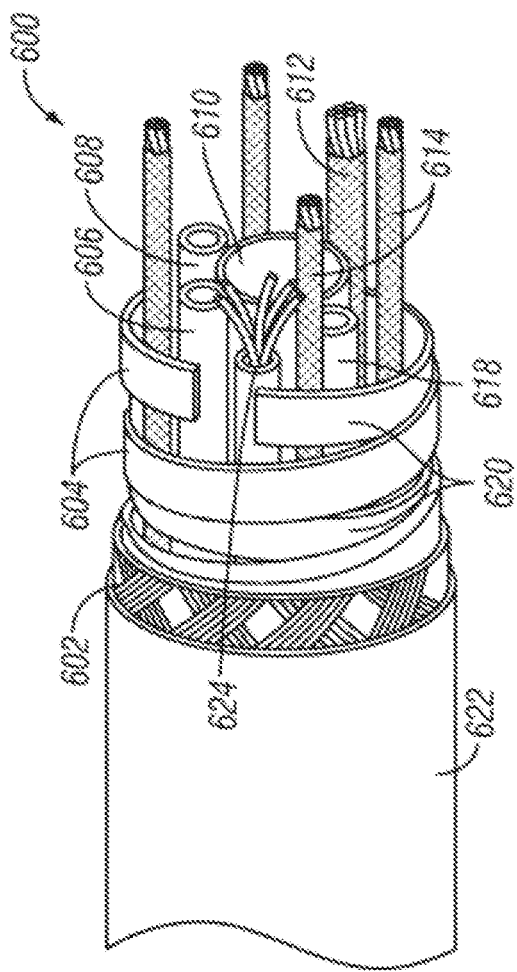
FIG. 6 illustrates a cutaway view of a flexible insertion tube.

FIG. 6 illustrates a cutaway view of a flexible insertion tube, indicated generally at 600, which includes four angulation wires 612, a wire for variable stiffness 612, various special purpose channels, an optical system, and protective sheathing. The special purpose channels include a water channel 606, air channel 608, biopsy/suction channel 610, and water jet channel 618. The optical system includes sensor/light package and signal, power, and ground wires 624. A light emitting diode (LED) or a laser diode (LD) light source (not shown) may be embedded in the distal end of the insertion tube and powered by the optical system wires 624. However, in some embodiments, the diode light source may be replaced with a fiber optic light guide bundle that runs the length of the insertion tube and is illuminated by a light source contained within the control head or control body. The angulation wires 612 are arranged in two sets of wire pairs that are oriented along an x- and y-axis respectively. Inner 620 and outer 604 spiral metal bands are wound in opposite directions to help translate torque from the angulation wires 612 along the long axis of the tube, as well as to protect the special purpose channels and optical system. A flexible stainless steel wire mesh 602, coated by a polymer outer layer 622, protects the spiral bands and contents. The polymer outer layer 622 is made of a biomaterial that seals the tube and its contents from liquids and features a smooth surface in order to minimize trauma as the insertion tube passes through the body.

In operation, rotation of an angulation knob via the control body shortens or lengthens one wire of a wire pair with respect to the other wire, thus causing the distal end of the flexible insertion tube to bend in a particular direction along the axis defined by the wire pair.

Figure 7:
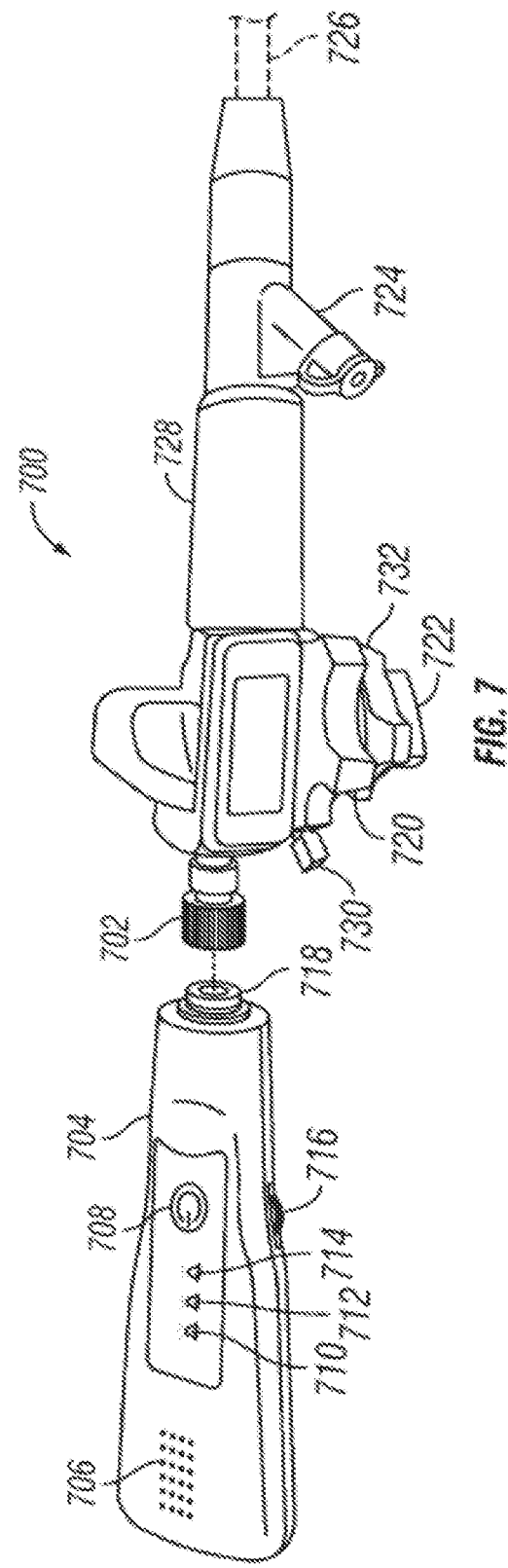
FIG. 7 illustrates a detachable wireless endoscope control head connected to an endoscope control body via an interface in accordance with one embodiment.

FIG. 7 illustrates a detachable wireless endoscope control head connected to an endoscope control body via an interface in accordance with one embodiment. The wireless endoscope system is indicated generally at 700, and includes a wireless control head 704, an endoscope control body 728, and an insertion tube 726. The endoscope control body 728 is comprised of angulation knobs (720 and 732), an angulation lock 722, a therapeutic instrument insertion port 724, and a control coupling 702. The control head 704 is comprised of a control button 708, device status indicators (710, 712, and 714), a speaker 706, a control dial 716, and a control port 718 suitable for connection to the control coupling 702. Because the presence and configuration of angulation knobs and componentry vary for each type of endoscope, other embodiments may feature an endoscope control body that omits some of the above features or includes other features not listed herein.

The control button 708 is used to power the device on or off. Depressing the control button for a preset period of time toggles the power state. In some embodiments, the control button may also control the illumination level of the specialized observation and illumination optical system (not pictured). Depressing the control button for a preset time period (different than the time period for power) cycles through levels of magnification or demagnification for the optical system. The method by which the control button powers on or powers off the device control circuitry, or the method by which the control button controls the level of illumination of the specialized observation and illumination optical system, is programmable and can be customized. Alternative embodiments may include multiple buttons, toggles, slide switches, touch screen controls, or programmable relays (i.e., a remote device that connects to and controls the device).

Device status indicators 710, 712, and 714 are visible on the control head 704. As depicted, the device status indicators are implemented using light emitting diodes (LED) directly wired to the control circuitry. The device status indicators may change colors or flash on and off according to a predefined pattern in order to signal different states. However, in alternative embodiments, the device status indicators may be implemented in hardware using an embedded programmable display, via software by transmitting status events (e.g., a battery status event or network status event) to a wirelessly connected device via an API, or by any other visual, auditory, or tactile method of alerting a user of a change in device status.

Some embodiments of the endoscope 728 may be connected to an air and water source via the air/water insertion port 730. The control body 728 may have an aeration/perfusion button (not shown), a suction button shown, angulation knobs (720 and 732), an angulation lock 722, and a therapeutic instrument insertion port 724. The aeration/perfusion button is pressed in order to instruct aeration or perfusion. The suction button is pressed in order to suck fluid. The angulation knob is manipulated in order to bend the bending section. The presence and configuration of angulation knobs and componentry vary for each type of endoscope.

Figure 8:
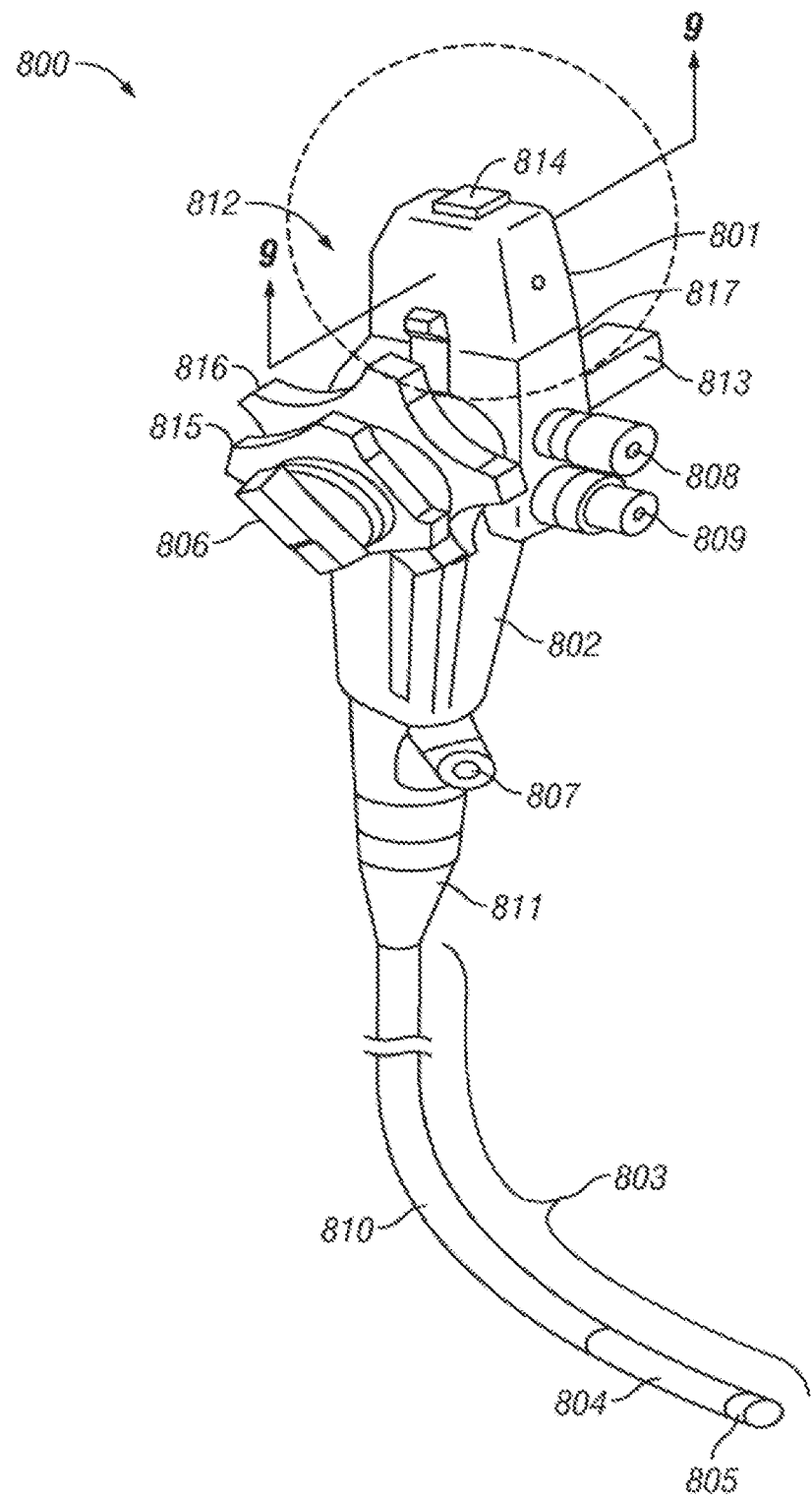
FIG. 8 illustrates a perspective view showing a fully-encapsulated wireless endoscope control unit in accordance with one embodiment.

FIG. 8 illustrates a perspective view showing a fully encapsulated wireless endoscope control unit in accordance with one embodiment and indicated generally at 800. The wireless video endoscope 812 includes an elongated insertion tube 803 and a control body 802. The insertion tube 803 is flexible (soft). The control body 802 is coupled to the proximal end of the insertion tube 803. The wireless control head 801 is extended from the lateral part of the control body 803. The insertion tube 807 has an anti-insertion tube breakage member 811, which is made of an elastic material, fixed to the proximal end thereof. The anti-insertion tube breakage member 811 prevents abrupt bend of a joint that is joined to the control body 802.

The insertion tube 803 comprises a flexible tube 810, a bending section 804, and a distal part 805. The flexible tube 810 is flexible and soft. The bending section 804 is fixed to the distal end of the flexible tube 810 and can be bent remotely using the control body 802 and the angulation knobs 806. The distal part 905 is fixed to the distal end of the bending section 804. An observation optical and illumination optical system (not shown) are incorporated in the distal part 807. This specialized observation and illumination optical system 804 contains cabling that runs the length of the insertion tube 803 and through the control body 802, ultimately linking to control circuitry (described in more detail in FIG. 13) in the wireless control head 801. An aeration/perfusion nozzle, a suction port, and a fluid supply port are bored in the distal part 807. When a manipulation is made in order to aerate or perfuse the endoscope, cleaning fluid or gas is jet out to an optical member located on the outer surface of the observation optical system through the aeration/perfusion nozzle. The suction port is bored in the distal end of a therapeutic instrument passage channel run through the insertion tube 803. Fluid is jetted out to an object to be observed through the fluid supply port. The therapeutic instrument passage channel is used to pass a therapeutic instrument into a body cavity or suck fluid therefrom.

Some embodiments of the endoscope 812 may be connected to an air and water source via the air/water insertion port 813. This allows for the usage of the aeration/perfusion button 808 and the suction button 809. The control body 802 has an aeration/perfusion button 808, a suction button 809, an angulation knob 806, a wireless control head 801, a remote-control switch 814, and a therapeutic instrument insertion port 807. The aeration/perfusion button 808 is pressed in order to instruct aeration or perfusion. The suction button 809 is pressed in order to suck fluid. The angulation knob 806 is manipulated in order to bend the bending section 804. The presence and configuration of angulation knobs and componentry vary for each type of endoscope. The remote-control button 814 is used to power the wireless control head 801 and control brightness of the camera LEOs. The therapeutic instrument insertion port 807 is an opening that opens onto the therapeutic instrument passage channel.

In alternative embodiments, the control body 802 may also feature a hanging apparatus comprising a hook, looped hook, spring-loaded closable hook, ring, or any other suitable mechanism for suspending the endoscope from an overhang during operation or cleaning.

Figure 9:
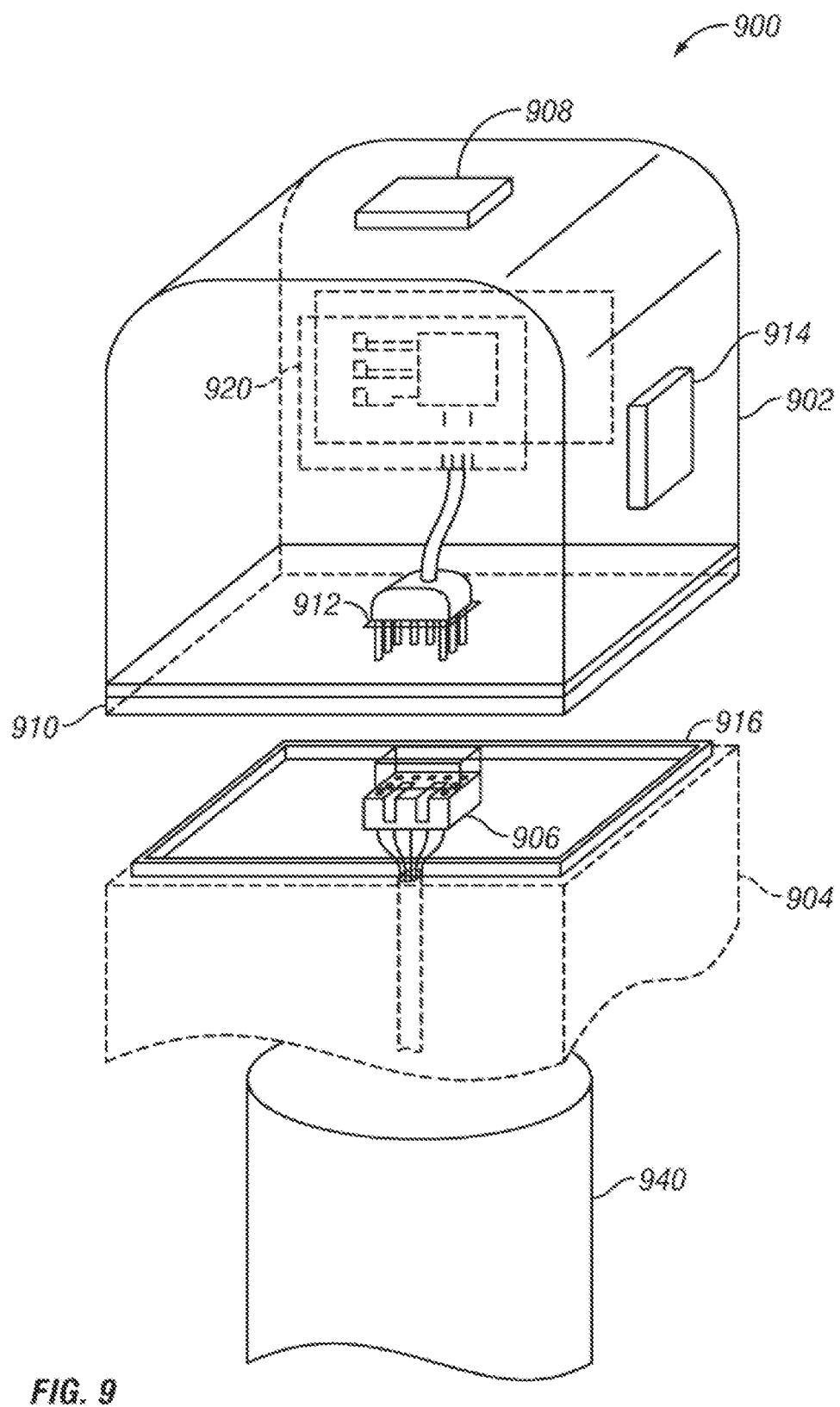
FIG. 9 illustrates a cutaway view of a wireless endoscope control head in perspective for use in a fully-encapsulated wireless endoscope control unit.

FIG. 9 illustrates a cutaway view of an exemplary wireless endoscope control head in perspective for use in a fully-encapsulated wireless endoscope control unit. The fully-encapsulated control unit, indicated generally at 900, includes a control head 902 that contains control circuitry 920, control buttons (908 and 914), an optical system interface comprising a type-A interface connector 912 that is configured to mate with a type-B interface connector 906, and a specially-designed lip 916 for hermetically sealing the control head 902 to the control body 904. The type-A and -B interface connectors can be implemented using any mated electronic connectors that carry sufficient lines to support the optical system interface as described below. The type-A connector 912 connects to the control circuitry 920, and the type-B connector 906 serves as a terminal for the signal, power, and ground lines carried via the insertion tube 940 from the optical system located in the distal end. The control circuitry 920 and the optical system interface are shown in more detail in FIG. 13.

Figure 10:
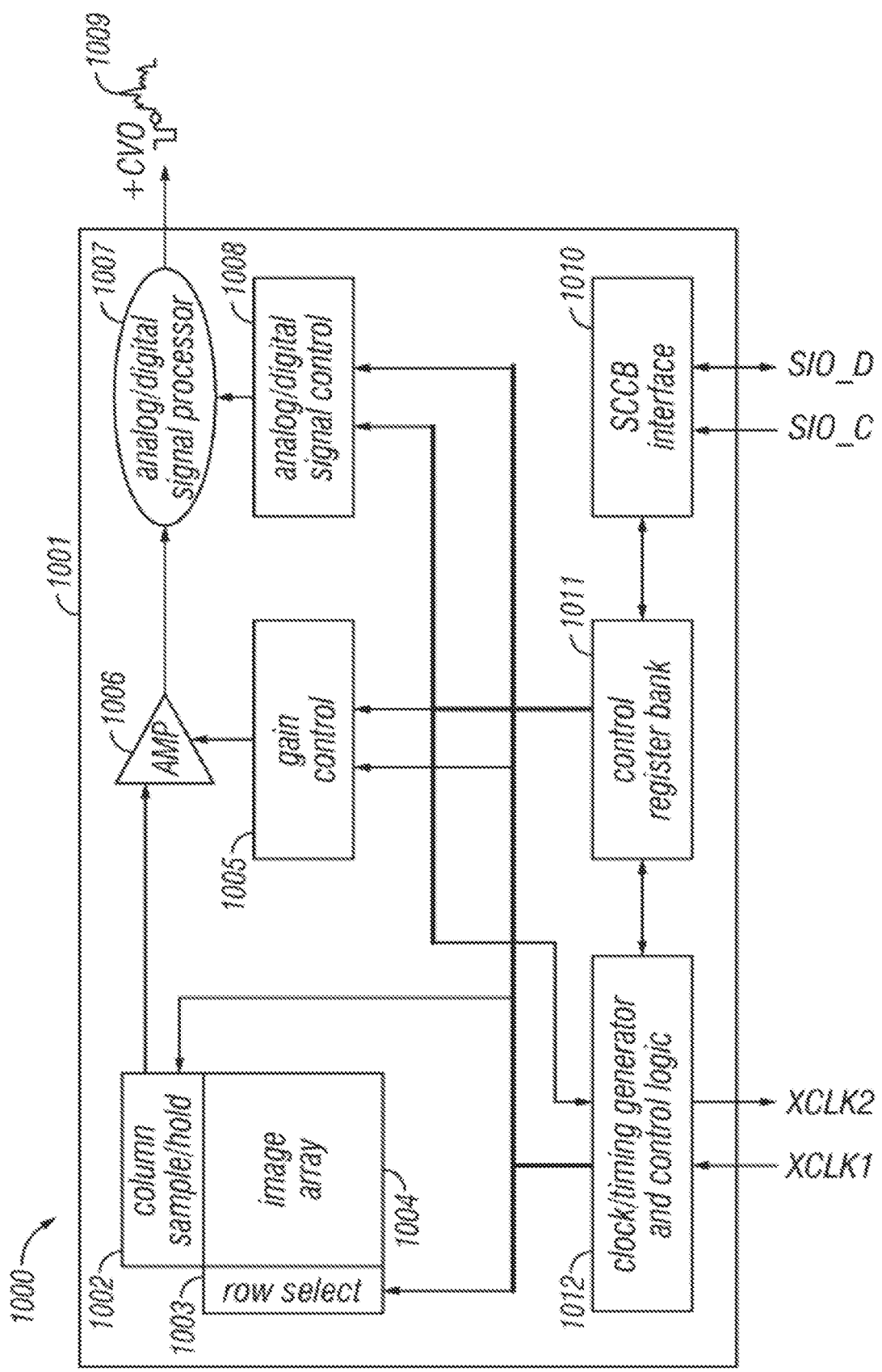
FIG. 10 is a block diagram illustrating an image sensor circuit in accordance with one embodiment.

FIG. 10 is a block diagram illustrating an image sensor circuit in accordance with one embodiment, indicated generally at 1000. The image sensor circuit 1000 includes an image array 1004, analog/digital signal processor 1007, analog/digital signal control 1008, clock/timing generator and control logic 1012, control register bank 1011, and a serial camera control bus (SCCB) interface 1010. A pattern is captured on the light sensor array and stored in the image array 1004.

In operation, the image array 1004 is integrated row by row starting with the upper left-hand pixel in the array 1004. When an integration period begins, the timing generator and control logic circuit 1012 will reset all of the pixels in a row before progressing to the next row in the array 1004. In embodiments featuring analog output, the control circuitry will transfer the integrated value of each pixel to a correlated double sampling (CDS) circuit and then to a shift register bank. After the shift register bank has been loaded, the pixel information will be serially shifted one pixel at a time to the analog video amplifier 1006. The gain of this amplifier 1006 is controlled by gain control 1005. In embodiments featuring a digital readout, the image sensor features an analog-to-digital converter for every column, and conversion is conducted in parallel for each pixel in a row. A flesh-tone balancing algorithm may be applied to the pixels at this stage. After the gain and offset values are set in the video amplifier 1006, the pixel information is then passed to the analog-to-digital signal processor 1007 where it is rendered into a digital signal 1009. Subsequently, the digital image data is further processed to remove sensing defects.

Windowing may be implemented directly on the chip through the timing and control circuit 1012, which enables any size window in any position within the active region of the array to be accessed and displayed with one-to-one pixel resolution. Windowing can be used for on-chip control of electronic pan, zoom, accelerated readout, and tilt operations on a selected portion or the entire image. In some embodiments, the image sensor 1000 may include progressive and interlaced scan readout modes. In alternative embodiments, the image sensor 1000 may include other auxiliary circuits that enable on-chip features such as image stabilization and image compression.

The image sensor 1000 may be implemented using a CCD, CMOS, NMOS, PMOS, or other suitable sensor for use with producing digital video (e.g., MPEG-4). The image sensor 1000 is connected to signal, power, and ground wires are long enough to connect the distal end of the insertion tube with the optical system interface.

Figure 11:
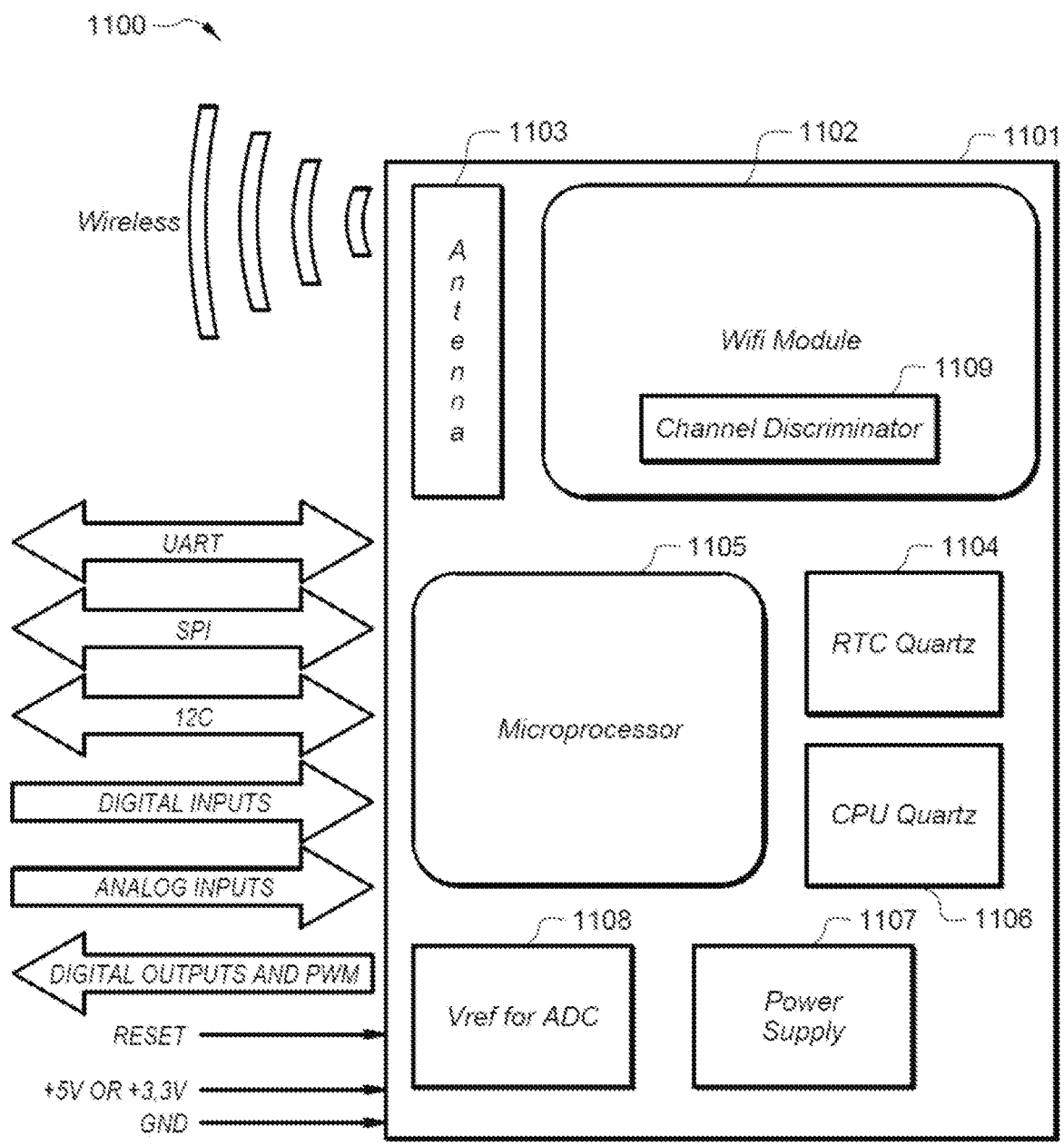
FIG. 11 is a block diagram illustrating the wireless module of a control circuit for a wireless endoscope in accordance with one embodiment.

FIG. 11 is a block diagram illustrating the wireless module of a control circuit of a wireless endoscope in accordance with one embodiment, indicated generally at 1100. The wireless module includes an antenna 1103, a transmit/receive module 1102, a microprocessor 1105, a real-time clock 1104, a CPU clock 1106, a power supply 1107, and a voltage reference for analog/digital conversion 1108. In some embodiments, the microprocessor 1105 also includes a channel hopping mechanism that uses one or more channel discriminators 1109 to control the manner in which the wireless module hops among potentially available RF channels, so as to substantially reduce and optimally minimize the likelihood of RF interference from other devices operating within the same band or adjacent bands.

The communication protocol of the wireless module 1100 may be implemented using widely adopted consumer standards such as 802.11 (Wi-Fi) and 802.15.1 (Bluetooth). In other embodiments, the wireless communication protocol may be implemented using a custom protocol stack, including media access control (MAC) and a physical layer implementation (PHY). To protect sensitive patient data in flight, communication over the wireless connection may be secured using channel or protocol level encryption such as WEP, WPA, AES, or SSL. However, at-rest data protection may also be implemented by encrypting the operational data on chip and requiring connected devices to decrypt the data upon receipt. For video only operational data, the application layer protocol may be implemented using popular consumer standards, such as the IP camera protocol. In other embodiments, the application layer may be implemented using a proprietary protocol that incorporates other operational data, such as symbolic data (see FIGS. 16 and 17), and includes device or user authentication.

Figure 12:
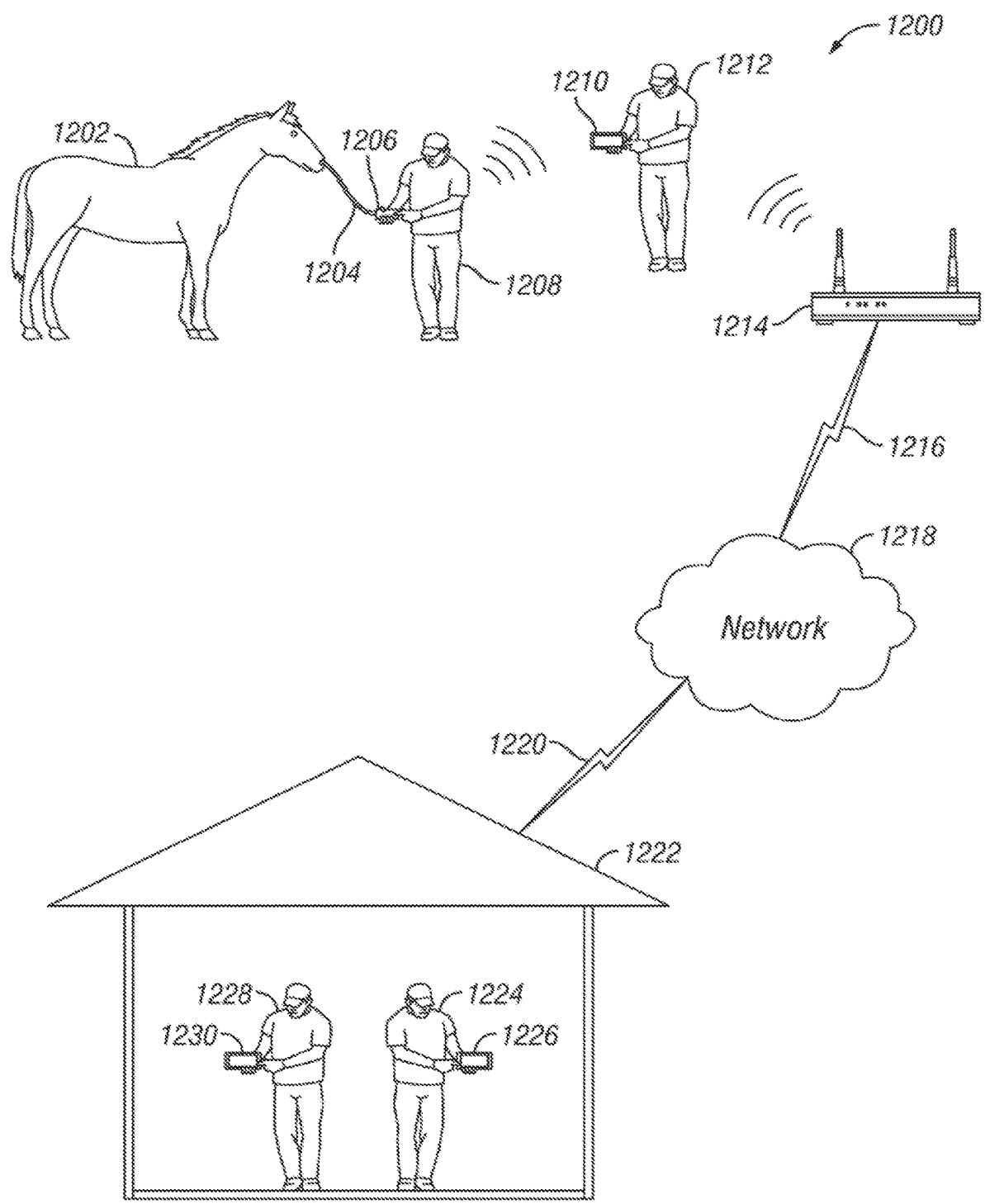
FIG. 12 illustrates a system for transmitting operational data from an endoscopy procedure to a plurality of devices in accordance with one embodiment.

FIG. 12 illustrates a system for transmitting operational data from an endoscopy procedure to a plurality of devices in accordance with one embodiment. The system, indicated generally at 1200, includes a wireless endoscope 1206, a patient 1202, a monitoring device 1210, operators (1208 and 1212), observers (1224 and 1228) with remote devices (1226 and 1230), a network 1218, and a network relay 1214. As depicted, the patient 1202 is a horse; however, a patient may be any human or animal that is examined or operated on using an endoscope. Examples of such operations are provided below in Table 1. The monitoring device 1210 may be implemented using a television, a smart phone, a tablet, a laptop, a desktop computer, a wearable device (e.g., a head-mounted display), or any computer system configured to communicate with the wireless endoscope that is capable of presenting operational data to an operator. The network 1218 may be implemented using a local area network (LAN), wide area network (WAN), wireless personal area network (WPAN), mesh network, or any other suitable network topology for relaying data over a distance. The network relay may be implemented using a wireless router, a cellular router that connects to a local personal area network as well as a cellular WAN, or any other network hardware or software that is configured to communicate with the wireless module of the endoscope 1206 and relay data across the network 1218. The network relay 1214 is connected to the network 1218 via a network connection 1216 by cellular, cable, fiber, telephone, satellite, or any other medium for transmitting digital data over a distance. The remote location 1222 includes any indoor or outdoor location that is beyond the effective radio transmission range of the wireless endoscope 1206 because of distance, obstruction, or interference. The remote devices (1226 and 1230) may comprise any combination of a television, a smart phone, a tablet, a laptop, a desktop computer, a wearable device (e.g., a head-mounted display), or any computer system configured to communicate with the wireless endoscope that is capable of presenting operational data to an operator.

In operation, a patient 1202 is examined or operated upon using the wireless endoscope 1206 by inserting a flexible or rigid insertion tube 1204. The wireless endoscope 1206 transmits operational data to connected monitoring devices (1208, 1210, 1226, and 1230). Remote devices (1226 and 1230) are connected to the wireless endoscope 1206 indirectly via the relay 1214 and the network 1218 via network connections (1216 and 1220).

Remote monitoring of an endoscopy procedure provides yet another advantage of the many embodiments by enabling classrooms or seminars to participate in a live operation. This opens up new possibilities where only a passive review of prerecorded operations was previously possible. Clinical studies may be expanded beyond centralized operational facilities to remote sites, such as a battlefield, emergency clinic, or even a barn. When coupled with the operational data sharing method discussed in detail below, the remote networking capabilities enable new and useful telemedicine applications. For example, an experienced physician could oversee multiple concurrent off-site operations conducted by junior physicians, and provide operational feedback through his monitoring device.

Figure 13:
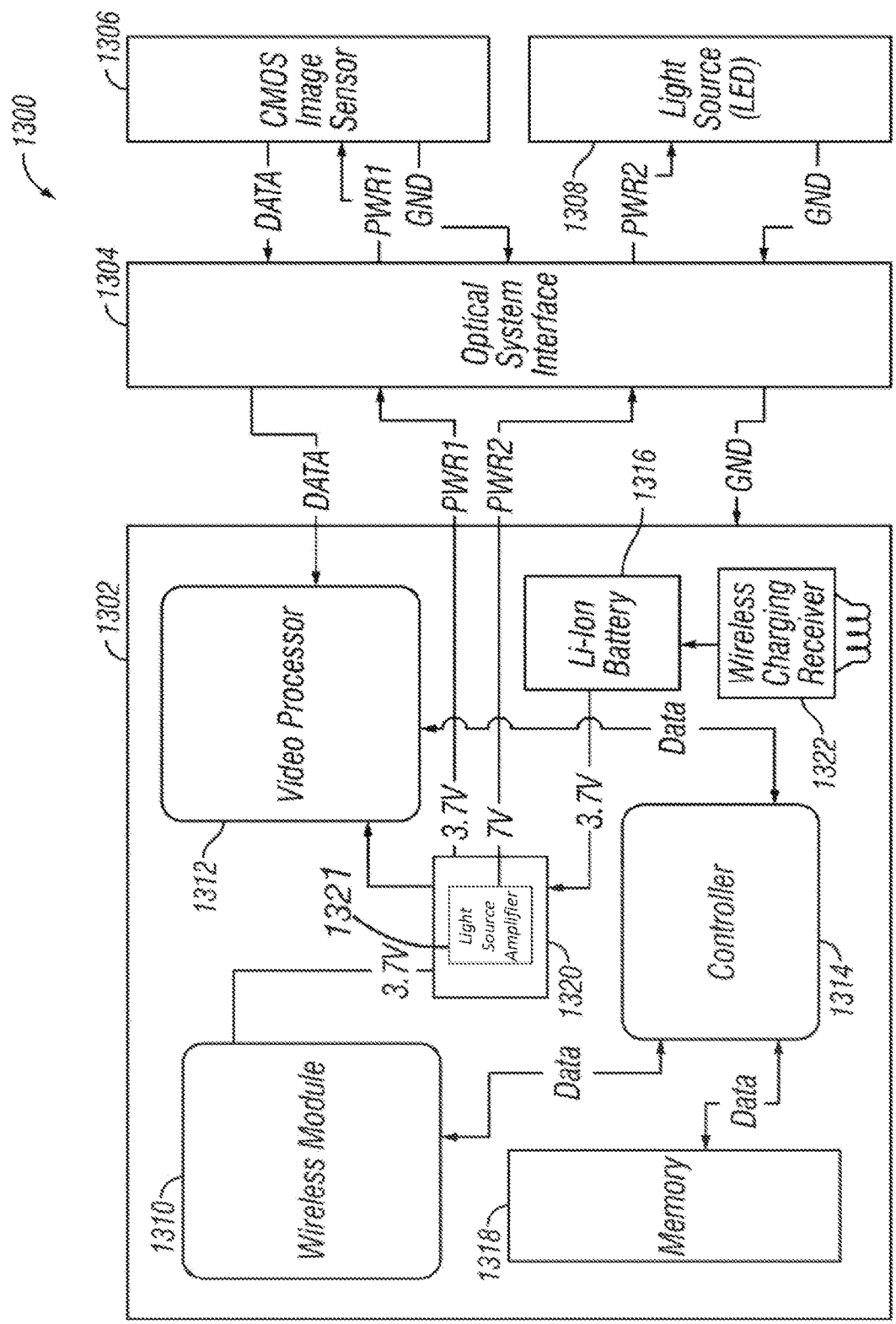
FIG. 13 is a block diagram illustrating the control logic for a wireless endoscope in accordance with one embodiment.

FIG. 13 is a block diagram showing control logic for a wireless endoscope in accordance with one embodiment. The control logic, indicated generally at 1302, includes a wireless module 1310, a video processor 1312, a microcontroller 1314, a battery 1316, a wireless charging receiver 1322, a memory 1318, and a voltage regulator 1320. The wireless module 1310 (described in detail in FIG. 11) transmits and receives operational data to and from monitoring devices. The image sensor 1306 captures digital image data through a lens system embedded in the distal tip of the endoscope insertion tube. The image sensor 1306 may be implemented using a CCD, CMOS, or other image sensor as depicted in FIG. 10. The video processor 1312 captures image data from the image sensor 1306, converts it into a video format, and applies any post-capture image processing. The video processor 1312 comprises hardware or software logic for video encoding, image compression, stabilization, magnification, or any other post-capture digital signal processing (DSP). The microcontroller 1314 coordinates functionality between the video processor 1312, the wireless module 1310, and the memory 1318. The microcontroller 1314 may be implemented using a prefabricated solution, such as an Arduino or TinyDuino board, or any other integrated circuit comprising a processor core, memory, and programmable input/output peripherals. The battery 1316 is optimally lithium-ion (Li-Ion), but may be implemented using any rechargeable battery technology that features a compact form factor relative to an endoscope control body. The wireless charging receiver 1322 features charging coils and an inductive charging circuit that may conform to industry standards such as the Qi interface standard promulgated by the Wireless Power Consortium. The memory 1318 provides a secondary cache beyond what is available in the microcontroller 1314, and may be implemented with any volatile memory technology, such as static random access memory (SRAM) or dynamic random access memory (DRAM). In some embodiments, the memory 1318 may be implemented using a solid state drive or flash memory so as to provide permanent storage capabilities when the device is powered off. The voltage regulator 1320 provides power to the various components by stepping up or stepping down voltage from the battery 1316 as needed. In some embodiments, the voltage level for the light source 1308 may be much greater than what other logic boards or circuits can safely handle. Thus, the voltage regulator 1320 may include a light source amplifier 1321 that can serve as a brightness booster to provide additional illumination capability to the optical system.

The optical system interface 1304, which is housed in the control head (depicted in FIG. 9), connects the image sensor 1306 and the light source 1308 to control circuitry 1302 in the control head. The optical system interface 1304 provides power to the image sensor 1306 and light source 1308. Data from the image sensor 1306 is relayed to the control logic 1302 via the optical system interface 1304. The data portion of the optical system interface 1304 may be implemented using any number of signal and control lines depending on the optimal data bus width (likely dependent on image sensor size and frame rate needs).

In operation, a light lens at the distal end of the insertion tube emits the light onto a subject within the body. A camera lens then focuses the light reflected from the illuminated subject onto an image sensor 1306 housed in the distal end. The image sensor 1306 records the captured light as image or video data and transmits the data to the video processor via the optical system interface 1304. The video processor 1312 applies post-capture processing, such as stabilization or magnification, to the raw data before compressing it using a codec, such as H.264, MPEG-4, LZO, FFmpeg, or HuffYUV. The video processor 1312 sends the processed data to the controller 1314, which may buffer it in the memory 1318. The controller 1314 forwards the processed data to the wireless module 1310 for transmission to connected devices. In some embodiments, the memory 1318 may be implemented using a shared memory directly connected to the various components.

In addition to the many advantages, a fully portable endoscopy system presents new challenges, such as device power and transportation. A conventional system, as illustrated in FIG. 1, could be easily powered by plugging the monitoring equipment directly into an electrical socket. Transporting such a conventional system was limited because the system was only portable to the extent that the monitoring equipment could be wheeled from one room to another. In contrast, a truly portable endoscope enables off-site operation, the success of which is predicated on safe and efficient transportation of sensitive medical equipment.

Figure 14:
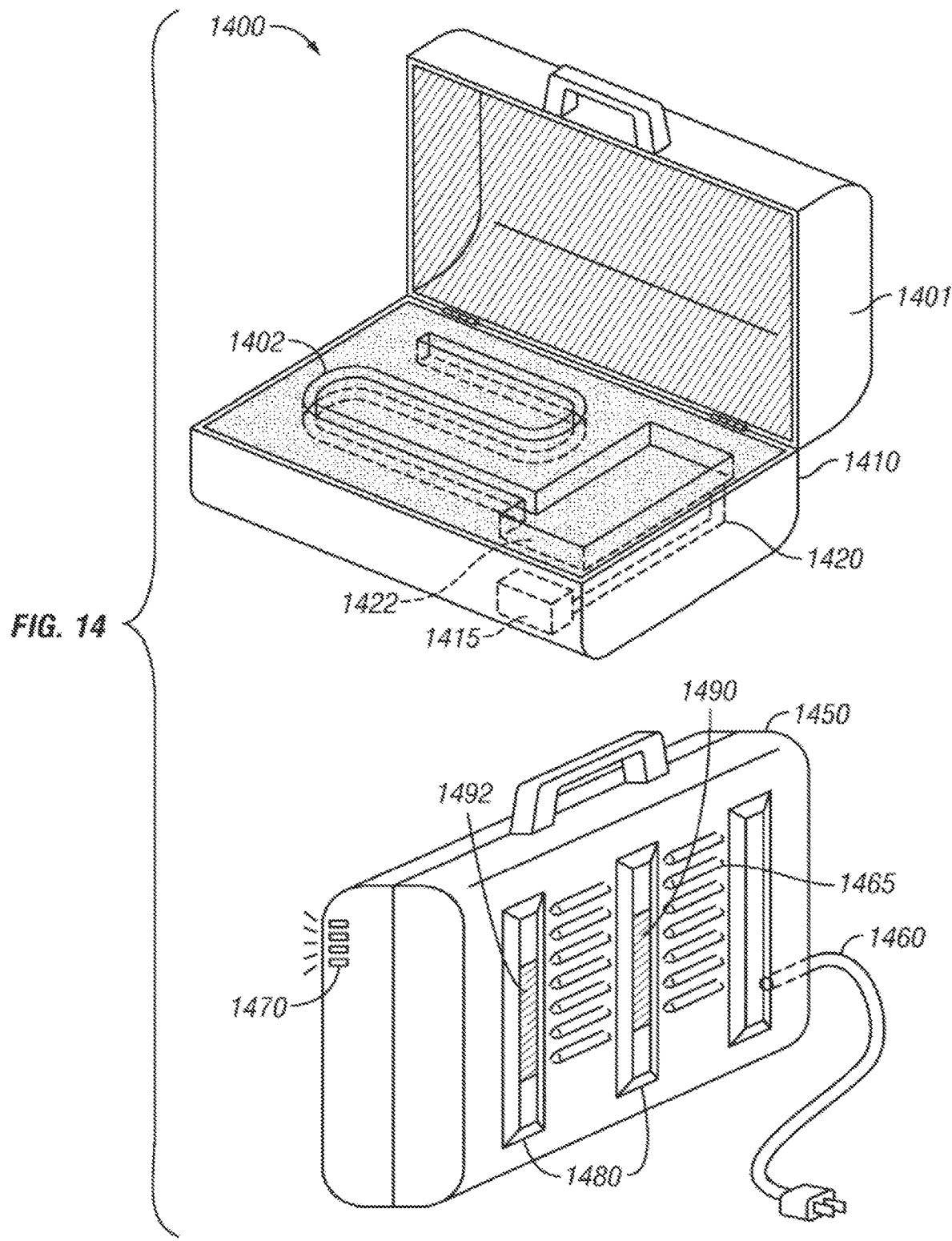
FIG. 14 illustrates a perspective view of a carrying case, in opened and closed configurations, for stowing and charging a wireless endoscopy system.

Consequently, a system is presented for stowing and charging a wireless endoscope in accordance with the many embodiments. FIGS. 14A and 14B illustrate perspective views of an exemplary carrying case, in opened and closed configurations, for stowing and charging a wireless endoscopy system. FIG. 14A illustrates an opened carrying-case, indicated generally at 1400, that includes an outer shell 1410, molded force-dampening material 1402, an inductive charging plate 1422, and power management circuitry 1415. The outer shell 1410 may be formed of any suitably lightweight, rigid, durable material, such as aluminum, ceramic, plastic, or resin, that has adequate tensile, flexural, and compressive strength to withstand sudden impacts of 1000 N or more. The force-dampening material 1402 absorbs and dissipates sudden impact forces applied to the outer shell 1410. The force-dampening material 1402 is optimally comprised of flame retardant polyurethane foam, molded with recesses or cavities to match the contours of a wireless endoscope. However, the force-dampening material 1402 may be formed using any suitable material that dissipates force away from the stowed device and is not highly flammable. A high-frequency inductive power transmission pad 1422, comprising ultra-thin transmission coils, is nested within the portion of the force-dampening material 1402 that receives the control head and control body of the wireless endoscope. The power management circuitry 1415, when connected to a power source, manages charging of the wireless endoscope by monitoring temperature, charging duration, and device battery level. The power management circuitry is connected to the power transmission pad 1422 via control and power lines 1420. If the temperature in the case reaches an unsafe operating level (e.g., greater than 50 degrees Celsius), the power management circuitry 1415 is designed to disable inductive charging. In some embodiments, the outer shell may contain ventilation ducts 1465 that allow air to flow through the case. In other embodiments, the recess in the force dampening material 1422 for the endoscope control unit may be lined with conductive sheets (designed to maximize surface area) connected to a large conductive surface area on the exterior of the case for conducting heat away from the interior of the case.

FIG. 14B illustrates a closed carrying case in accordance with one embodiment, indicated generally at 1450, that includes a charging cable 1460, battery level or charging status indicators 1470, stacking guides 1480, ventilation ducts 1465, and electrodes 1490 and 1492. The charging cable 1460 is designed to be plugged into a 120-240V wall outlet; however, some embodiments may feature a swappable cable that can be powered by a 12V outlet commonly found in vehicles. The battery level indicators 1470 may be implemented using LEDs, which are illuminated when the device is charged, charging, or dead, or which estimate current device battery levels according to the number of LEDs illuminated. Alternatively, the battery level indicators 1470 may be implemented using an LCD or LED display or other suitable mechanism for displaying status information.

In some embodiments, the power management circuitry 1415 may include a radio unit to monitor battery level status and charging notifications broadcast from the wireless module of the endoscope according to a proprietary protocol operating in frequency bands allocated for consumer electronics (e.g., the "S" band). Changes in battery level or charging state are reflected on the outside of the case via battery level or charging status indicators 1470.

In other embodiments, the carrying case may be stacked with other carrying cases. Stacking guides 1480 are comprised of a pattern of protrusions on the top of the case, matched with corresponding recesses on the bottom of the case. The stacking guides 1480 may be designed as parallel linear ridges as depicted in FIG. 14B, or as other patterns such as a cross or L-shapes. When two or more cases are laid flat and stacked vertically, the stacking guides 1480 should prevent the cases from becoming easily decoupled by application of a horizontal force. Alternatively, the ridges and recesses of the stacking guides 1480 may form an interlocking pattern (e.g., interlocking trapezoidal ridges), such that one case may be attached to another by sliding the recesses of one case along the interlocking ridges of the other.

In alternative embodiments, the outer shell 1410 may feature conductive pads, an anode 1490 and a cathode 1492, which when connected to a second case, form a charging network. The anode 1490 and cathode 1492 are connected to the power management control circuitry 1415. When the charging cable 1460 provides power to the first case, and the anode 1490 and cathode 1492 provide power to the second case. The orientation and size of the conductive pads should be designed in such a way so as to avoid accidental electrical shock when several cases are being charged.

FIGS. 15A, 15B, and 15C show several views illustrating the wireless transmission of operational data to a variety of devices, indicated generally at 1500. FIG. 15A illustrates a perspective view of a wireless endoscope 1564 transmitting operational data, over a wireless connection 1566, gathered via a flexible insertion tube 1562. FIG. 15B illustrates a cross-sectional view of the distal end 1536 of the flexible insertion tube 1562 inserted within a body cavity 1532. The distal end 1536 captures operational data and transmits the data feed over the wireless connection 1566 to connected devices, such as a smart device 1510 or a head-mounted display 1504. FIG. 15C illustrates a two-dimensional view of operational video data 1502, streamed from the wireless endoscope 1564, and viewable on the various connected devices. A smart device, such as a phone or tablet, can display the operational video data 1502 via an embedded high-resolution display. In contrast, a head-mounted display 1504 projects high-resolution images directly into the operator's retina via a lens 1508.

Figure 16:
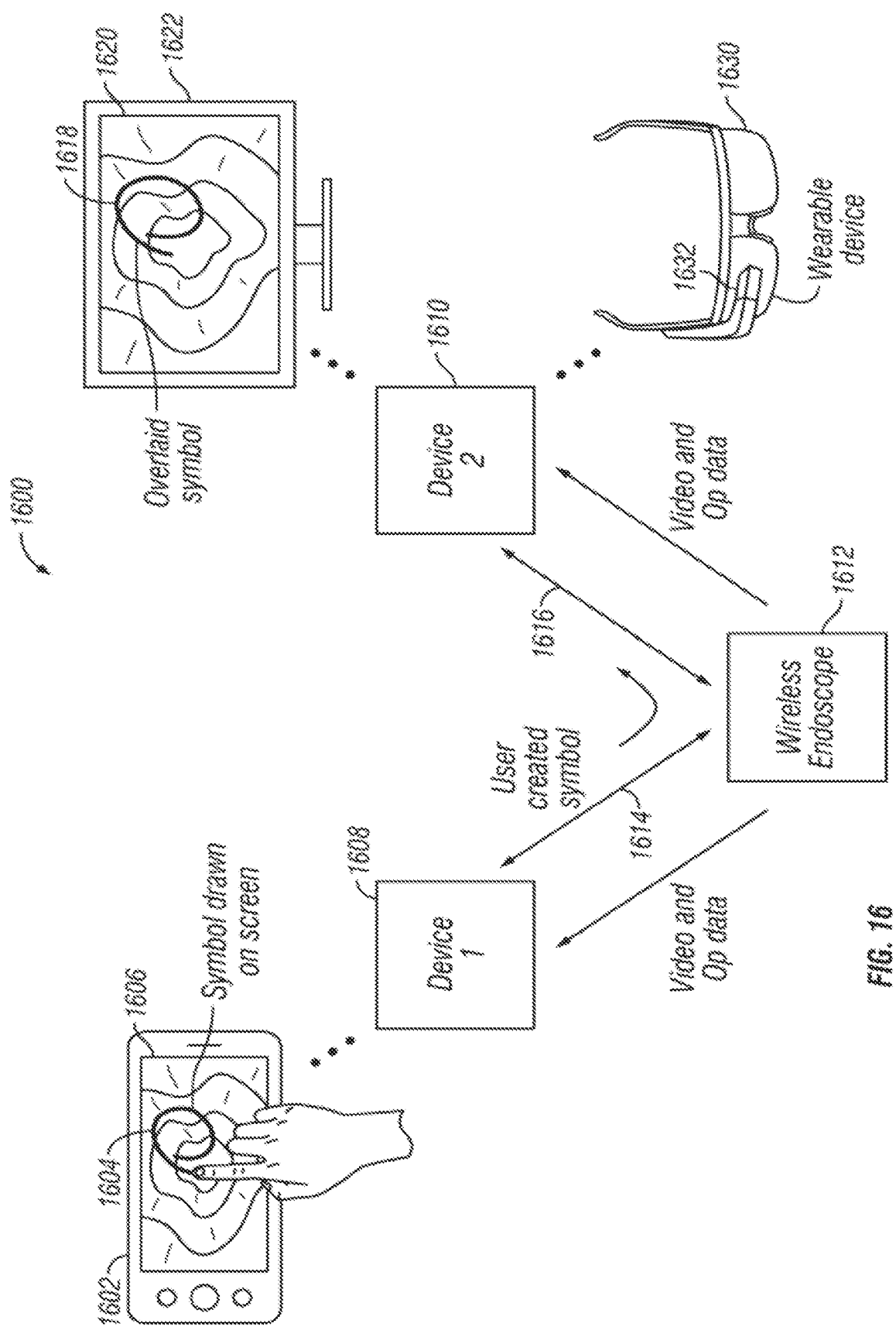
FIG. 16 is a data flow diagram illustrating a method of sharing operational data sharing across multiple devices.

FIG. 16 is a data flow diagram illustrating a method of sharing operational data sharing across multiple devices, indicated generally at 1600, that comprises a first 1608 and a second device 1610 wirelessly connected to a wireless endoscope 1612. A device may be a smart phone 1602, a tablet, a laptop, a desktop computer 1622, a wearable device 1630 (e.g., a head-mounted display), or any computer system configured to communicate with the wireless endoscope 1612 that is capable of presenting operational data to an operator.

The method 1600 begins with a wireless endoscope 1612 establishing a wireless connection with at least two devices. The sensor package of the wireless endoscope 1612 then begins to gather operational data. In some embodiments, this may consist of a high-resolution video feed captured by the optical system. In other embodiments, operational data may comprise stereoscopic video (for use with a 3D display), thermal imaging, or multichannel intraluminal impedance (pH monitoring). The wireless endoscope 1612 simultaneously broadcasts the operational data to the several connected devices. To ensure adequate medical privacy, the operational data is encrypted, or is transmitted over encrypted channels. During the operation, an observer using a first device 1608 of the several connected devices creates a symbol 1604 on the first device 1608 in response to operational data presented to the observer. A symbol may be any digital image, video, audio, text, or structured data. For example, an operator could create a symbol 1604 by drawing a figure on a touch screen device 1602. Or, an operator could create a symbol by recording video or audio commentary to be streamed alongside other operational data. Such a use has particular application in telemedicine or education and may make use of a network relay as depicted in FIG. 12. The symbol 1604 is then transmitted to a second device 1610 from the several connected devices via the wireless endoscope 1612. The symbol 1604 is then presented to the operator of the second device 1610 alongside other operational data.

In alternative embodiments, an operator may be a remote computer system that transmits a symbol 1604, comprising previously recorded operational data, to be presented and compared alongside current operational data. Of course, transmission of the symbol 1604 may be shared among connected devices without routing operational data through the wireless endoscope 1612.

In some alternative embodiments, the selection of common commercial standards effectively transforms the wireless endoscope 1612 into a medical device platform that enables a wide array of customizable viewing options while greatly reducing equipment costs. For example, wireless connectivity may be implemented using widely adopted consumer standards such as 802.11 (Wi-Fi) and 802.15.1 (Bluetooth) to enable non-proprietary, commercially available consumer devices, such as Google Glass® or Oculus Rift®, to be connected to the wireless endoscope 1612. Head-mounted displays enable a physician operator to view two- or three-dimensional video data while keeping both hands free to operate the endoscope. Two-dimensional video data may be streamed over the wireless connection using popular protocols like internet protocol camera (IP camera). These commercial devices, which are not marketed for medical purposes, have the additional advantage of being much less costly than typical medical imaging devices that are subjected to extensive FDA review.

Figure 17:
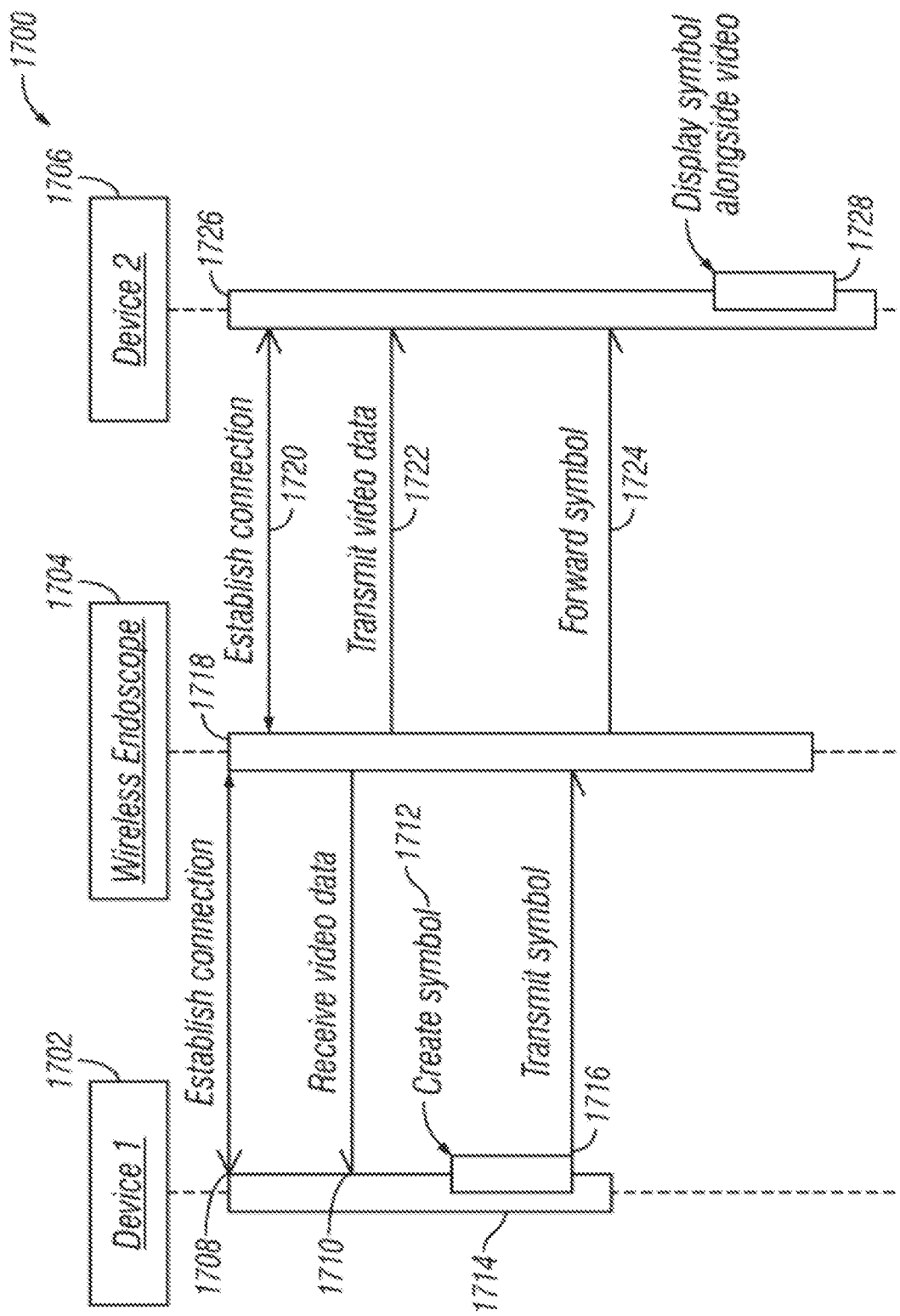
FIG. 17 is a sequence diagram illustrating a method of sharing operational data across multiple devices.

FIG. 17 is a sequence diagram illustrating a method of sharing operational data across multiple devices, indicated generally at 1700. The method begins at step 1708, in which a first device 1702 establishes a wireless connection with a wireless endoscope 1704. Next, a second device 1706 connects to the wireless endoscope 1704 at step 1720. The lifelines 1714, 1718, and 1726 for the data sharing operation extend until the connection closes. In step 1710, the first device 1702 receives video data from the wireless endoscope 1704. The wireless endoscope also transmits video data in parallel to the second device 1706 at step 1722.

In step 1712, an operator creates a symbol on the first device 1702, which is then transmitted to the wireless endoscope 1704 in step 1716 over the wireless connection. Then, in step 1724, the wireless endoscope 1704 forwards the symbol to the second device 1706 over a wireless connection. Finally, at step 1728, the second device 1706 displays the transmitted symbol alongside the video data.

While the data sharing of 1700 is represented as occurring in sequence, operational data, including video and symbol data, may be continuously broadcast over data packets that are not guaranteed to arrive in order. Subsequent software- or hardware-based processing on the connected devices may reorder the packets according to the proper time sequence, and correlate presentation of the data so it appears synchronously. Because operational data must be presented in real-time, lost or significantly delayed packets may be dropped altogether, resulting in reduced frame rate or signal quality degradation.

Figure 18A:
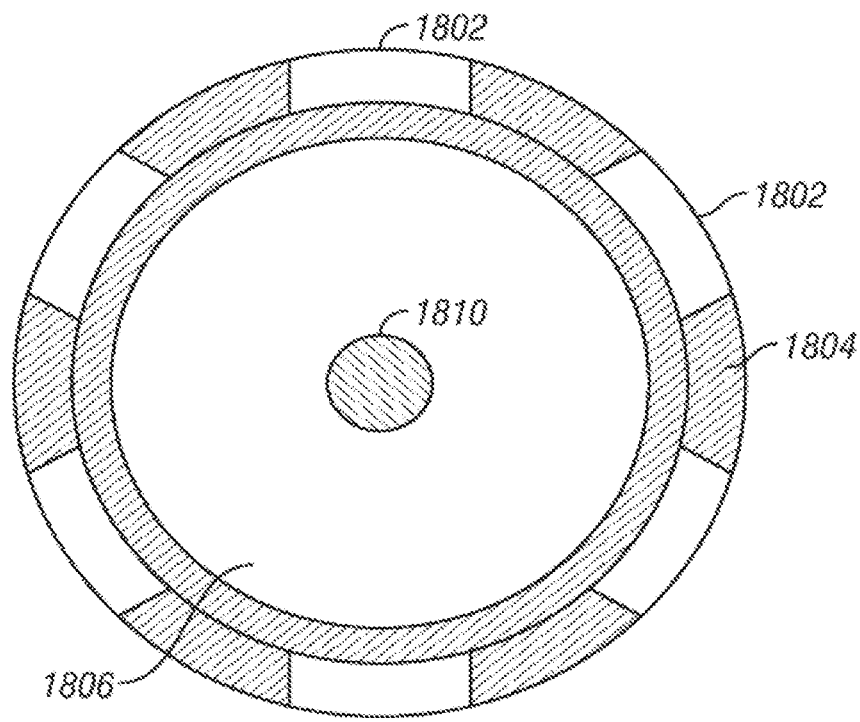
FIGS. 18A and 18B show several views illustrating an optical system in accordance with one embodiment.
Figure 18B:
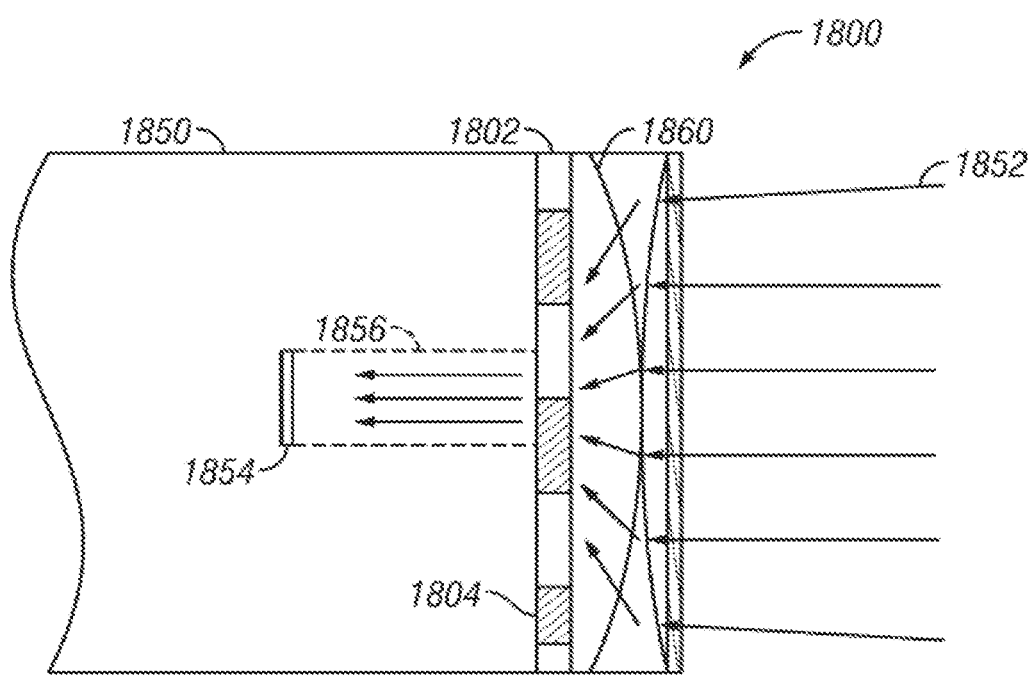

FIGS. 18A and 18B show several views illustrating the distal end of an optical system in accordance with one embodiment. FIG. 18A shows a planar view of the distal end of an exemplary optical system. The optical system includes an aperture 1810 within a diaphragm 1806 that is encircled by one or more light emitters 1802 surrounded by light shielding material 1804. The light emitters 1802 may be comprised of light emitting diodes (LED), laser diodes (LD), infrared emitting diodes (IRED), fiber optic light guides, or any suitable compact light source that can be embedded within an endoscope insertion tube. A lens system (illustrated in FIG. 18B) seals the optical system from fluids.

Because some of the light emitted from the light emitters 1802 will reflect off of the lens system, light shielding material 1804 is used to insulate the image sensor (not shown), nested within the aperture 1810, from overexposure. The light shielding material 1804 may be putty, plastic, tape, or any suitable material for preventing light from reflecting off of the lens system into the aperture 1810.

In alternative embodiments, the outer area of the lens system that covers the light emitters 1802 may be polarized differently than the inner area of the lens system to help reduce reflective interference.

FIG. 18B shows a side view of an exemplary optical system, indicated generally at 1850, that includes a lens system 1860, light emitters 1802, light shielding material 1804, an image sensor 1854, and a sensor chamber 1856. Light emitted from the optical system 1850 reflects off of the subject under observation to form an image (illustrated as light rays 1852). The light rays 1852 are focused by the lens system 1860 through the aperture 1810 onto the image sensor 1854.

Capabilities of the present invention extend, but are not limited, to such devices as bronchoscopes (examination of air passages and the lungs), colonoscopies (colon), gastroscopes (small intestine, stomach, and esophagus), arthroscopes (joints), hysteroscopes (uterus), and cystoscopes (urinary tract and bladder). Table 1, below, further illustrates some of the procedures that may be conducted using one or more of the foregoing embodiments.

TABLE 1

| Procedure | Description |
| --- | --- |
| Arthroscopy | Examination of the joints |
| Bronchoscopy | Examination of the air passages and the lungs |
| Colonoscopy | Examination of the colon |
| Colposcopy | Examination of the cervix and the tissues of the vagina and vulva |
| Cystoscopy | Examination of the urinary bladder |
| EGO (Esophageal Gastroduodenoscopy) | Examination of the esophagus, stomach, and duodenum |
| ERCP (endoscopic retrograde cholangio-pancreatography) | Examination of the liver, gallbladder, bile ducts, and pancreas |
| Fetoscopy | Examination of the fetus |
| Laparoscopy | Examination of the abdominal cavity via small incision |
| Laryngoscopy | Examination of the back of the throat, including the voice box (larynx) and vocal cords |
| Proctoscopy | Examination of the rectum and the end of the colon |
| Rhinoscopy | Examination of the inside of the nose |
| Thoracoscopy | Examination of the lungs or other structures in the chest cavity |
| Hysteroscopy | Examination of the uterus |
| Cystoscopy | Examination of the urinary tract and bladder |

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, a description of a technology in the "Background of the Invention" is not to be construed as an admission that certain technology is prior art to any embodiment(s) in this disclosure. Neither is the "Summary of the Invention" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

In light of the foregoing disclosure, I claim:

1. A system for wirelessly transmitting data from an endoscope, the system comprising:
   the endoscope having a control body and an insertion tube extending from the control body;
   an image sensor located at the distal end of the insertion tube;
   a light source located at the distal end of the insertion tube; and
   a control head connected to the control body, having:
      a battery;
      a light source amplifier connected to the battery, the light source amplifier operable to boost the intensity of the light source;
      a video processor configured to create video data from a video stream captured via the image sensor; and
      a single wireless communication module configured for both wireless transmitting and receiving and comprising a channel discriminator that controls the manner in which the wireless communication module hops among available RF channels to reduce RF interference during said transmitting and receiving, wherein the single wireless communication module is configured to:
         negotiate a wireless connection with at least a first mobile device and a second mobile device,
         transmit the video data to the first mobile device over the wireless connection,
         receive, from the first mobile device over the wireless connection, a symbol created on the first mobile device using the video data received from the wireless communication module, and
         after receiving the created symbol from the first wireless device, wirelessly transmit the created symbol and the video data over the wireless connection to the second mobile device, different than the first mobile device, such that said second mobile device can display the created symbol alongside the video data.

2. The system of claim 1, wherein the wireless communication module is further configured to negotiate a second wireless connection with the second device and to simultaneously transmit the video data to the second device over the second wireless connection.

3. The system of claim 1, wherein the wireless communication is configured to broadcast the video data to at least two wireless mobile devices.

4. The system of claim 1, further comprising a relay configured to wirelessly connect to the wireless communication module and to forward the video data over a network.

5. The system of claim 1, wherein data transmitted over the wireless connection is encrypted.

6. The system of claim 1, wherein the mobile device comprises a touch screen.

7. The system of claim 1, wherein the mobile device is a wearable device.

8. The system of claim 1, further comprising a power management module configured to monitor the charge level of the battery, wherein the power management module is further configured to broadcast the charge level of the battery via the wireless communication module.

9. The system of claim 1, wherein the control head further comprises a light source illumination level controller.

10. The system of claim 1, wherein the control head further comprises a battery level indicator.

11. The system of claim 1, wherein the control head further comprises a device status indicator configured to provide a visual, auditory, or tactile alert to alert a user of a change in device status.

12. The system of claim 1, wherein the insertion tube is flexible.

13. The system of claim 1, wherein the insertion tube is rigid.

14. The system of claim 1, further comprising a hanging apparatus coupled to the system.

15. The system of claim 1, wherein the control head is coupled with the control body to form a hermetic seal.

16. The system of claim 1, wherein the battery is inductively charged.

17. The system of claim 1, wherein the control head is contained in a separate enclosure and is attached to the control body via an interface.

18. The system of claim 1, wherein the control head is directly and rigidly connected to the control body.

* * * * *